US006869965B2

(12) United States Patent
Gordeev et al.

(10) Patent No.: US 6,869,965 B2
(45) Date of Patent: Mar. 22, 2005

(54) ANTIMICROBIAL QUINOLONE DERIVATIVES AND USE OF THE SAME TO TREAT BACTERIAL INFECTIONS

(75) Inventors: Mikhail F. Gordeev, Castro Valley, CA (US); Dinesh V. Patel, Fremont, CA (US); Michael R. Barbachyn, Kalamazoo, MI (US); James R. Gage, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/729,816

(22) Filed: Dec. 5, 2003

(65) Prior Publication Data

US 2004/0215017 A1 Oct. 28, 2004

Related U.S. Application Data

(62) Division of application No. 09/996,927, filed on Nov. 29, 2001, now Pat. No. 6,689,769.
(60) Provisional application No. 60/257,904, filed on Dec. 21, 2000.

(51) Int. Cl.$^7$ ................... A61K 31/47; A61K 31/421; C07D 221/02; C07D 263/04
(52) U.S. Cl. ................... 514/312; 514/376; 546/112; 546/183; 548/229
(58) Field of Search ................... 548/229; 546/112; 546/183; 514/312, 376

(56) References Cited

U.S. PATENT DOCUMENTS

| | | | |
|---|---|---|---|
| 3,669,965 A | 6/1972 | White | 260/250 A |
| 3,769,295 A | 10/1973 | Hoyle et al. | 260/307 |
| 4,065,463 A | 12/1977 | Beck et al. | 260/307 |
| 4,283,403 A | 8/1981 | Davenport | 424/263 |
| 4,382,892 A | 5/1983 | Hayakawa et al. | 260/243.3 |
| 4,563,459 A | 1/1986 | Grohe et al. | 514/254 |
| 4,620,007 A | 10/1986 | Grohe et al. | 546/156 |
| 4,705,799 A | 11/1987 | Gregory | 546/209 |
| 4,801,600 A | 1/1989 | Wang et al. | 514/376 |
| 4,921,869 A | 5/1990 | Wang et al. | 514/376 |
| 4,948,801 A | 8/1990 | Carlson et al. | 514/307 |
| 4,977,173 A | 12/1990 | Brittelli et al. | 514/376 |
| 4,985,557 A | 1/1991 | Hayakawa et al. | 540/598 |
| 5,053,407 A | 10/1991 | Hayakawa et al. | 514/230.2 |
| 5,130,316 A | 7/1992 | Carlson et al. | 514/255 |
| 5,142,046 A | 8/1992 | Hayakawa et al. | 544/105 |
| 5,164,510 A | 11/1992 | Brickner | 548/231 |
| 5,254,577 A | 10/1993 | Carlson et al. | 514/376 |
| 5,523,403 A | 6/1996 | Barbachyn | 544/137 |
| 5,654,435 A | 8/1997 | Barbachyn et al. | 546/271.4 |
| 5,861,413 A | 1/1999 | Häbich et al. | 546/157 |
| 6,124,334 A * | 9/2000 | Hutchinson | 514/376 |

FOREIGN PATENT DOCUMENTS

| | | | |
|---|---|---|---|
| DE | 27 55 061 | 6/1978 | C07D/471/04 |
| DE | 31 42 854 A1 | 5/1983 | C07D/401/04 |
| DE | 32 48 505 A1 | 7/1984 | C07D/401/04 |
| DE | 32 48 507 A1 | 7/1984 | A01N/43/42 |
| DE | 196 01 265 A1 | 7/1997 | C07D/9/547 |
| EP | 0 047 005 A1 | 3/1982 | C07D/498/06 |
| EP | 0 206 283 A2 | 12/1986 | C07D/498/06 |
| EP | 0 390 215 A2 | 10/1990 | C07D/413/12 |
| EP | 0 693 491 A1 | 1/1996 | C07D/413/04 |
| EP | 0 694 543 A1 | 1/1996 | C07D/413/04 |
| EP | 0 694 544 A1 | 1/1996 | C07D/413/04 |
| EP | 0 697 412 A1 | 2/1996 | C07D/417/04 |
| ES | 2 077 490 | 11/1995 | C07D/215/56 |
| JP | 57088182 | 6/1982 | C07D/498/06 |
| JP | 58072589 | 4/1983 | C07D/498/06 |
| JP | 2-69478 | 3/1990 | C07D/413/04 |
| WO | WO 93/09103 | 5/1993 | C07D/263/20 |
| WO | WO 94/13649 | 6/1994 | C07D/263/20 |
| WO | WO 98/07708 | 2/1998 | C07D/261/04 |
| WO | WO 99/41244 | 8/1999 | C07D/261/04 |
| WO | WO 00/10566 | 3/2000 | C07D/261/12 |

OTHER PUBLICATIONS

Gregory et al., "Antibacterials. Synthesis and Structure–Activity Studies of 3–Aryl–2–oxooxazolidines. 1. The "B" Group," *J. Med. Chem.*, 32:1673–1681 (1989).

Hayakawa et al., "Synthesis and Antibacterial Activities of Substituted 7–Oxo–2,3–dihydro–7H–pyrido[1,2,3–de][1,4] benzoxazine–6–carboxylic Acids," *Chem. Pharm. Bull.*, 32:4907–4913 (1984).

Kiely et al. "Synthesis of 7–(Alkenyl, Cycloalkenyl, and 1,2, 3,6–Tetrahydro–4–pyridinyl)quinilones," *J. Heterocyclic Chem.*, 28:1581–1585 (1991).

Mahmood et al., "Iron Lewis Acid Catalyzed Reactions of Aromatic Aldehydes with Ethyl Diazoacetate: Unprecedented Formation of 3–Hydroxy–2–arylacrylic Acid Ethyl Esters by a Unique 1,2–Aryl Shift," *J. Org. Chem.*, 63:3333–3336 (1998).

Newman, Paul, "Optical Remixture Procedures for Chemical Compounds, vol. 1; Amines and Related Compounds," Optical Remixture Information Center, Manhatten College, Riverdale, N.Y., 10471, 1978.

International Search Report dated Sep. 20, 2000.

* cited by examiner

*Primary Examiner*—Golam M M Shameem
(74) *Attorney, Agent, or Firm*—Pharmacia & Upjohn Company; Thomas A. Wootton

(57) ABSTRACT

Substituted quinolone derivatives in which an oxazolidinone, isoxazolinone, or isoxazoline is covalently bonded to a quinolone, methods of using the quinolone derivatives, and pharmaceutical compositions containing the quinolone derivatives are disclosed. Methods of synthesizing these substituted quinolone derivatives are also disclosed, and in particular a method of manufacturing a 7-(2-oxo-1,3-oxazolidin-3-yl)aryl-3-quinolinecarboxylic acid by condensing a 4-(2-oxo-1,3-oxazolidin-5-yl)aryl boronic acid with a 7-halo-quinolone derivative. The quinolone derivatives possess antibacterial activity, and are effective against a number of human and veterinary pathogens in the treatment of bacterial diseases.

5 Claims, No Drawings

ANTIMICROBIAL QUINOLONE DERIVATIVES AND USE OF THE SAME TO TREAT BACTERIAL INFECTIONS

CROSS-REFERENCE TO RELATED APPLICATION

This application claims the benefit of U.S. application Ser. No. 09/996,927 filed Nov. 29, 2001 now U.S. Pat. No. 6,689,769, which claim the benefit of U.S. provisional Application Ser. No. 60/257,904, filed Dec. 21, 2000.

FIELD OF THE INVENTION

The present invention relates to substituted quinolone derivatives wherein an oxazolidinone, isoxazolinone, or isoxazoline compound is chemically combined with a quinolone. The present invention also relates to a method of preparing pharmacologically active quinolone derivatives and various intermediates used in the method. The present quinolone derivatives are useful as broad spectrum antimicrobial agents effective against a number of human and veterinary Gram positive and Gram negative pathogens, including the Staphylococci, for example *S. aureus*; *Enterococci*, for example *E. faecalis*; *Streptococci*, for example *S. pneumoniae*; *Haemophilus*, for example *H. influenza*; *Moraxella*, for example *M. catarrhalis*; and *Escherichia* for example *E. coli*; *Mycobacteria*, for example *M. tuberculosis*; intercellular microbes, for example *Chlamydia* and *Rickettsiae*; and *Mycoplasma*, for example *M. pneumoniae*, amongst others. The present invention also relates to pharmaceutical compositions containing the quinolone derivatives, to methods of treating a bacterial infection using the quinolone derivatives, and to a process for producing the quinolone derivatives.

BACKGROUND OF THE INVENTION

The increase in bacterial resistance to existing antibacterial agents is a major clinical problem. Accordingly, there is a need in the art for compounds, compositions, and methods of treating warm-blooded animals that suffer from a bacterial infection and are resistant to conventional antibacterial treatments. The development and increase in resistance to the quinolone carboxylic acid class of antibacterial compounds has not been as pervasive as with other antibacterial agents. Therefore, new quinolone carboxylic acid compounds may be useful in combating resistant bacteria.

The 7-substituted quinolone carboxylic acid derivatives, represented by the general formula (II), wherein Y is either C—$R^5$ or N, and $R^1$ through $R^5$ include a wide variety of substituents, are well known as anti-fungal and anti-bacterial agents, and as synthetic intermediates to related compounds. The 7-substituted derivatives of compound (II) include the antibacterials cinoxacin (U.S. Pat. No. 3,669,965); ciprofloxacin (U.S. Pat. Nos. 4,563,459 and 4,620,007); ofloxacin (U.S. Pat. No. 4,382,892); and levofloxacin (U.S. Pat. Nos. 4,985,557, 5,053,407, and 5,142,046).

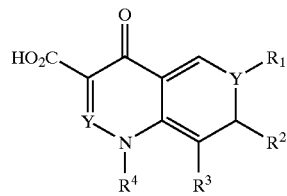

Oxazolidinones having a general structural formula (III) also are a well known class of orally active, synthetic antibacterial agents. The literature contains numerous references to oxazolidinones (III), wherein $R^1$ through $R^3$ include a wide variety of substituents. Oxazolidinones having one or two substituents on the phenyl ring are disclosed in U.S. Pat. Nos. 4,705,799; 5,523,403; and 5,654,435, for example. Oxazolidinones (III) include the antibacterial agent designated as DuP 721, see *J. Med. Chem.*, 32, 1673 (1989).

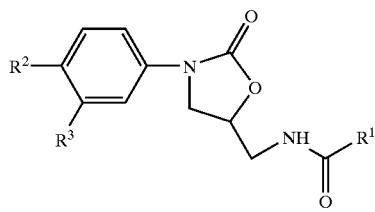

Oxazolidinones (III) having an arylbenzene substituent on the oxazolidinone ring are disclosed in U.S. Pat. Nos. 4,948,801 and 5,130,316. 3-[(Di- or fused-ring substituted) phenyl]-2-oxazolidinones are disclosed in U.S. Pat. Nos. 4,977,173; 4,921,869; 4,801,600; and 5,164,510. European Patent Applications 0 697 412; 0 694 544; 0 694 543; and 0 693 491, and International Patent Publication No. WO 93/09103, disclose 5- to 9-membered substituted aryl- and heteroaryl-phenyl oxazolidinones as antibacterial agents. U.S. Pat. No. 5,254,577 discloses aminomethyloxooxazolidinyl arylbenzene derivatives as antibacterial agents. Other references disclosing oxazolidinones include U.S. Pat. Nos. 4,801,600 and 4,921,869. Some of the pyridine-substituted phenyl oxazolidinone derivatives disclosed in the above patents are effective against Gram positive bacteria, such as *Staphylococcus aureus* and *Streptococcus pneumoniae*. However, the oxazolidinones are not active against Gram negative bacteria, such as *Escherichia coli, Klebsiella, Proteus*, and *Seratia marcenses*. Moreover, oxazolidinones cannot be administered as an injection solution because their free amino forms are sparingly soluble.

Isoxazolinone derivatives having a general structural formula (IV) are disclosed in WO 00/10566 as anti-bacterial agents. Simple isoxazolinones also are used as preemergent herbicides. For example, U.S. Pat. No. 4,065,463 discloses 2-methyl-4-(chloro-m-tolyl)-3-isoxazolin-5-one, which is useful in preventing weed growth.

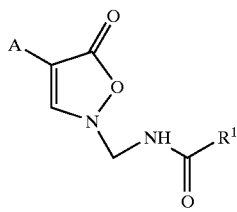

(IV)

Isoxazoline derivatives having a general structural formula (V) are disclosed in WO 99/41244, WO 98/07708 and U.S. Pat. No. 3,769,295 as anti-microbial agents. Simple isoxazolines also are used as preemergent herbicides. In addition, U.S. Pat. No. 4,283,403 discloses 3-aryl-2-isoxazolines, which are useful in preventing plant fungal diseases.

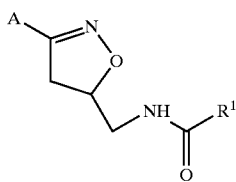

(V)

Although quinolones, oxazolidinones, isoxazolinones, and isoxazolines are known, applicants are aware of no reference which discloses covalently bonding a quinolone to an oxazolidinone, an isoxazolinone, or an isoxazoline, and using the resulting quinolone derivatives as broad spectrum anti-bacterial agents against both Gram positive and Gram negative bacteria.

The present invention is directed to structurally novel compounds produced by covalently bonding an antibacterial oxazolidinone, isoxazolinone, or isoxazoline compound to a substituted quinolone compound. The compounds of the present invention have a quinolone structure substituted with an oxazolidinone, isoxazolinone, or isoxazoline via a linking group at the 1- or 7-position of the quinolone.

The present compounds are active against Gram negative bacteria and Gram positive bacteria, and accordingly are useful as broad spectrum antibacterial agents. The present compounds are surprisingly effective against a number of human and veterinary pathogens, including *Staphylococci*, for example *S. aureus*; *Enterococci*, for example *E. faecalis*; *Streptococci*, for example *S. pneumoniae*; *Haemophilus*, for example *H. influenza*; *Moraxella*, for example *M. catarrhalis*; and *Escherichia* for example *E. coli*. Other examples include *Mycobacteria*, for example *M. tuberculosis*; intercellular microbes, for example *Chlamydia* and *Rickettsiae*; and *Mycoplasma*, for example *M. pneumoniae*. The present compounds also are envisioned as cytotoxic anticancer agents.

Syntheses of simple quinolone derivatives are well known in the art. However, the synthesis of a quinolone covalently linked to an oxazolidinone, an isoxazolinone, or an isoxazoline is not straightforward. Thus, a method of synthesizing compounds of the present invention also is disclosed.

SUMMARY OF THE INVENTION

One aspect of the present invention is to provide substituted quinolone derivatives having a structural formula (I):

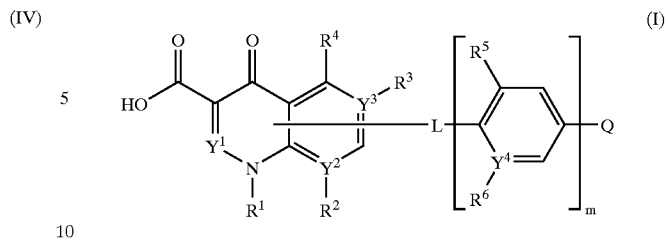

(I)

or a pharmaceutically acceptable salt, hydrate, or prodrug thereof, wherein $Y^1$ is CH or N;

$Y^2$, $Y^3$, and $Y^4$, independently, are C or N;

L is a bond or is a linker group attached to a carbon at the seven quinolone ring position or to an N at the one quinolone ring position, and selected from the group consisting of a bond, $NR^7$, and $NR^8(CR^9{}_2)_n NR^8$;

m is 0 or 1;

n is 0–3;

Q is selected from the group consisting of

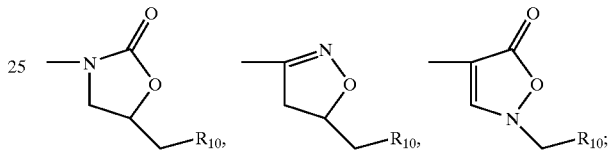

$R^1$ is selected from the group consisting of null, H, $C_1$–$C_4$alkyl, $C_3$–$C_5$cycloalkyl, $C_1$–$C_4$haloalkyl, and halophenyl;

$R^2$ is null when $Y^2$ is N, or is selected from the group consisting of H, alkyl, $C_1$–$C_2$alkoxy, halo, and haloalkoxy, when $Y^2$ is C, or when $Y^2$ is C, $R^1$ and $R^2$ can be taken together to form a 5- or 6-membered, optionally substituted, heteroalkyl or heteroaryl ring;

$R^3$ is H or F when $Y^3$ is C, or $R^3$ is null when $Y^3$ is N;

$R^4$ is selected from the group consisting of H, methyl, amino, and F; $R^5$ is selected from the group consisting of H, methyl, hydroxy, and halo;

$R^6$ is selected from the group consisting of H, methyl, hydroxy, and halo, when $Y^4$ is C, or $R^6$ is null when $Y^4$ is N;

$R^7$ is selected from the group consisting of H, $C_1$–$C_4$ alkyl, formyl, alkylcarbonyl, alkylsulfonyl, and alkoxycarbonyl;

$R^8$, independently, are H or $C_1$–$C_4$alkyl, or are taken together to form a 4- to 9-membered, optionally substituted, heteroalkyl or heteroaryl ring;

$R^9$, independently, are H or $C_1$–$C_4$alkyl, or are taken together to form a 4- to 9-membered heterocyclic or heterobicyclic ring, optionally substituted with $C_1$–$C_2$alkyl, haloalkyl, or methoximino;

$R^{10}$ is selected from the group consisting of OH, alkoxy, aryloxy, and $NHC(=Z)R^{11}$;

$R^{11}$ is selected from the group consisting of H, $C_1$–$C_7$alkyl, $C_3$–$C_5$cycloalkyl, hydroxymethyl, haloalkyl, $CH_2SMe$, $NR^{12}{}_2$, $C_1$–$C_4$alkoxy, and aryloxy;

$R^{12}$ is $C_1$–$C_4$alkyl; and

Z is O or S.

Another aspect of the present invention is to provide a pharmaceutical composition containing a compound of formula (I) and a pharmaceutical acceptable carrier, diluent, or excipient.

One other aspect of the present invention is to provide a method of treating microbial infections in a mammal comprising administering to the mammal a pharmaceutically effective amount of a compound of formula (I).

Another aspect of the present invention is to provide method of treating a cancer comprising administering to a mammal in need thereof a pharmaceutically effective amount of a compound of formula (I).

Yet another aspect of the present invention is to provide a method of manufacturing a compound of structural formula (I).

DETAILED DESCRIPTION OF THE PREFERRED EMBODIMENTS

As used herein, the terms and phrases have the meanings and definitions known in the art. Some of the more commonly used phrases are described in more detail below.

"Alkyl" refers to a cyclic, branched, or straight chain chemical group containing only carbon and hydrogen atoms, for example methyl, pentyl, and adamantyl. Alkyl groups can be unsubstituted or substituted with one or more substituents, e.g., halogen, alkoxy, acyloxy, amino, hydroxyl, mercapto, carboxy, benzyloxy, phenyl, and benzyl. Alkyl groups can be saturated or unsaturated (e.g., containing alkenyl or alkynyl subunits), at one or several positions. Typically, alkyl groups contain 1 to about 12 carbon atoms, for example 1 to about 10, or 1 to about 8-carbon atoms.

"Heteroalkyl" refers to a cyclic, branched, or straight chain chemical group containing carbon, hydrogen and at least one heteroatom. Heteroalkyl includes bicyclic compounds. The heteroatom typically is nitrogen, oxygen, or sulfur. Heteroalkyl groups can be unsubstituted or substituted with one or more substituents, e.g., halogen, alkoxy, acyloxy, amino, hydroxyl, mercapto, carboxy, benzyloxy, phenyl, and benzyl. When the heteroalkyl group contains a nitrogen atom, the nitrogen atom can be primary, secondary, tertiary, or quaternary, or can be in various forms such as an amide or sulfonamide. Heteroalkyl groups can contain one or more unsaturated (e.g., alkenyl or alkynyl) subunits. Typically, heteroalkyl groups contain 1 to about 12 atoms, for example 1 to about 8, or 1 to about 4 carbon atoms.

"Aryl" refers to a monovalent aromatic carbocyclic group having a single ring (e.g. phenyl), multiple rings (e.g. biphenyl), or multiple condensed rings (e.g. naphthyl or anthryl). Aryl groups can be unsubstituted or substituted with amino, hydroxyl, alkyl, heteroalkyl, alkoxy, halo, mercapto, and other substituents. Typically, the aryl group is a substituted single ring compound. For example, the aryl group is a substituted phenyl ring.

"Heteroaryl" refers to a monovalent aromatic group having a single ring (e.g., pyridyl or furyl) or multiple condensed rings (e.g., indolizinyl or benzothienyl) containing carbon atoms and having at least one heteroatom within the ring. The heteroatom preferably is nitrogen, oxygen or sulfur. Heteroaryl groups can be optionally unsubstituted or substituted with amino, hydroxyl, alkyl, heteroalky, alkoxy, halo, mercapto, and other substituents. In one embodiment, the heteroaryl group is substituted pyridyl.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "alkoxy" and "aryloxy" are defined as —OR, wherein R is alkyl or aryl, respectfully.

The term "hydroxy" is defined as —OH.

The term "amino" is defined as —NR$_2$, wherein each R, independently, is alkyl or hydrogen.

The term "alkylcarbonyl" is defined as R—C(=O)—, where R is alkyl.

The term "alkoxycarbonyl" is defined as RO—C(=O)—, where R is alkyl.

The term "alkylsulfonyl" is defined as R—SO$_3$, where R is alkyl.

The quinolone ring system is numbered as follows:

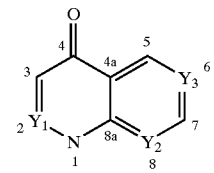

"Biologically active compounds" or "bioactive compounds" refers to present quinolone derivatives that exhibit biological activity. For instance, a biologically active compound can inhibit the interaction between an enzyme or receptor and its respective substrate(s) or endogenous ligand (s), or inhibit cell growth of a microorganism, by about at least 15% at a solution concentration of $10^{-3}$ molar or lower (i.e., has inhibitory activity). For example, a biologically active compound can inhibit such processes at solution concentrations of about $10^{-4}$ M or lower, preferably $10^{-5}$ M or lower, and more preferably about $10^{-6}$ M or lower.

The present invention is directed to quinolone-oxazolidinones, quinolone-isoxazolinones, and quilolone-isoxazolines of structural formula (I) as defined below:

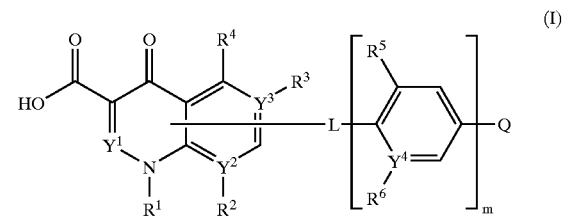

or a pharmaceutically acceptable salt, hydrate, or prodrug thereof, wherein $Y^1$ is CH or N;

$Y^2$, $Y^3$, and $Y^4$, independently, are C or N;

L is a bond or is a linker group attached to a carbon at the seven quinolone ring position or to an N at the one quinolone ring position, and selected from the group consisting of a bond, $NR^7$, and $NR^8(CR^9{}_2)_nNR^8$;

m is 0 or 1;

n is 0–3;

Q is selected from the group consisting of

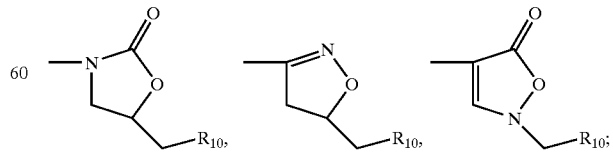

$R^1$ is selected from the group consisting of null, H, $C_1$–$C_4$alkyl, $C_3$–$C_5$cycloalkyl, $C_1$–$C_4$haloalkyl, and halophenyl;

$R^2$ is null when $Y^2$ is N, or is selected from the group consisting of H, alkyl; $C_1$–$C_2$alkoxy, halo, and haloalkoxy, when $Y^2$ is C, or when $Y^2$ is C, $R^1$ and $R^2$ can be taken together to form a 5- or 6-membered, optionally substituted, heteroalkyl or heteroaryl ring;

$R^3$ is H or F when $Y^3$ is C, or $R^3$ is null when $Y^3$ is N;

$R^4$ is selected from the group consisting of H, methyl, amino, and F; $R^5$ is selected from the group consisting of H, methyl, hydroxy, and halo;

$R^6$ is selected from the group consisting of H, methyl, hydroxy, and halo, when $Y^4$ is C, or $R^6$ is null when $Y^4$ is N;

$R^7$ is selected from the group consisting of H, $C_1$–$C_4$ alkyl, formyl, alkylcarbonyl, alkylsulfonyl, and alkoxycarbonyl;

$R^8$, independently, are H or $C_1$–$C_4$alkyl, or are taken together to form a 4- to 9-membered, optionally substituted, heteroalkyl or heteroaryl ring;

$R^9$, independently, are H or $C_1$–$C_4$alkyl, or are taken together to form a 4- to 9-membered heterocyclic or heterobicyclic ring, optionally substituted with $C_1$–$C_2$alkyl, haloalkyl, or methoximino;

$R^{10}$ is selected from the group consisting of OH, alkoxy, aryloxy, and NHC(=Z)$R^{11}$;

$R^{11}$ is selected from the group consisting of H, $C_1$–$C_7$alkyl, $C_3$–$C_5$cycloalkyl, hydroxymethyl, haloalkyl, $CH_2SMe$, $NR^{12}_2$, $C_1$–$C_4$alkoxy, and aryloxy;

$R^{12}$ is $C_1$–$C_4$alkyl; and

Z is O or S.

The compounds of the present invention are effective antimicrobial agents against a number of human and veterinary pathogens, including Gram-positive, Gram negative, and anaerobic bacteria, and in treating microbial infections in mammals. The present compounds also can be used as cytotoxic anticancer compounds.

Preferred compounds of general formula (I), are those wherein:

$Y^1$ is CH;

$Y^2$, $Y^3$, and $Y^4$ are C;

L is a bond or $NR^8(CR^9_2)_nNR^8$;

n is 2;

$R^3$ is H or F;

$R^4$ is H, methyl, amino, or F;

R and $R^6$, independently, are H, methyl, hydroxy, or halo;

$R^{10}$ is OH, alkoxy, aryloxy, or NHC(Z)$R^{11}$ when Q is an oxazolidinone or isoxazoline group, or is aryloxy, NHC(Z)$R^{11}$, when Q is a isoxazoline group; and Z is O.

A preferred Q is an oxazolidinone group. Preferred L-Q groups, wherein m is zero, are selected from the group consisting of:

wherein $R^{13}$ and $R^{14}$, independently, are H, $C_{1-2}$alkyl, or $C_{1-2}$ haloalkyl, or are taken together to form a cyclopropyl or methoximino group.

It also is preferred that compounds of formula (I) are optically pure enantiomers having the S-configuration at the five-position carbon of the oxazolidinone or isoxazoline ring.

Preferred compounds of the present invention include (Ac is C(=O)$CH_3$):

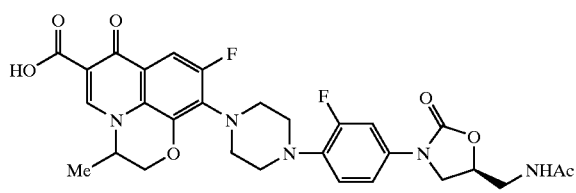

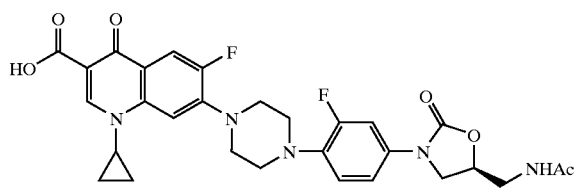

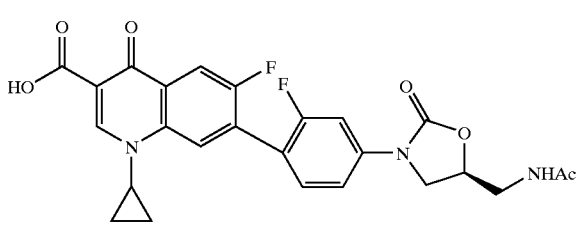

The present invention is also directed to methods of synthesizing pharmaceutically active oxazolidinone-, isoxazoline-, and isoxazolinone-substituted quinolones (I) and intermediate compounds used in the synthesis. The substituted quinolone derivatives of the present invention can be prepared by the following general synthetic schemes.

Scheme 1 illustrates one general method of synthesizing the 7-oxazolidinone-, isoxazoline-, and isoxazolinone-substituted quinolone compounds (B) of the present invention. Scheme 2 illustrates specific examples of synthesizing oxazolidinone-substituted quinolone compounds (3 and 6) of the present invention.

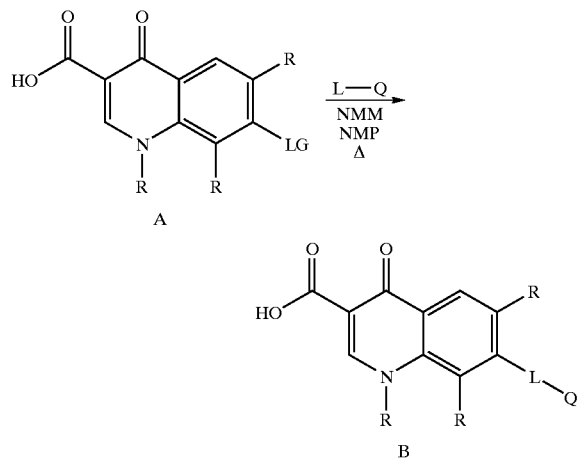

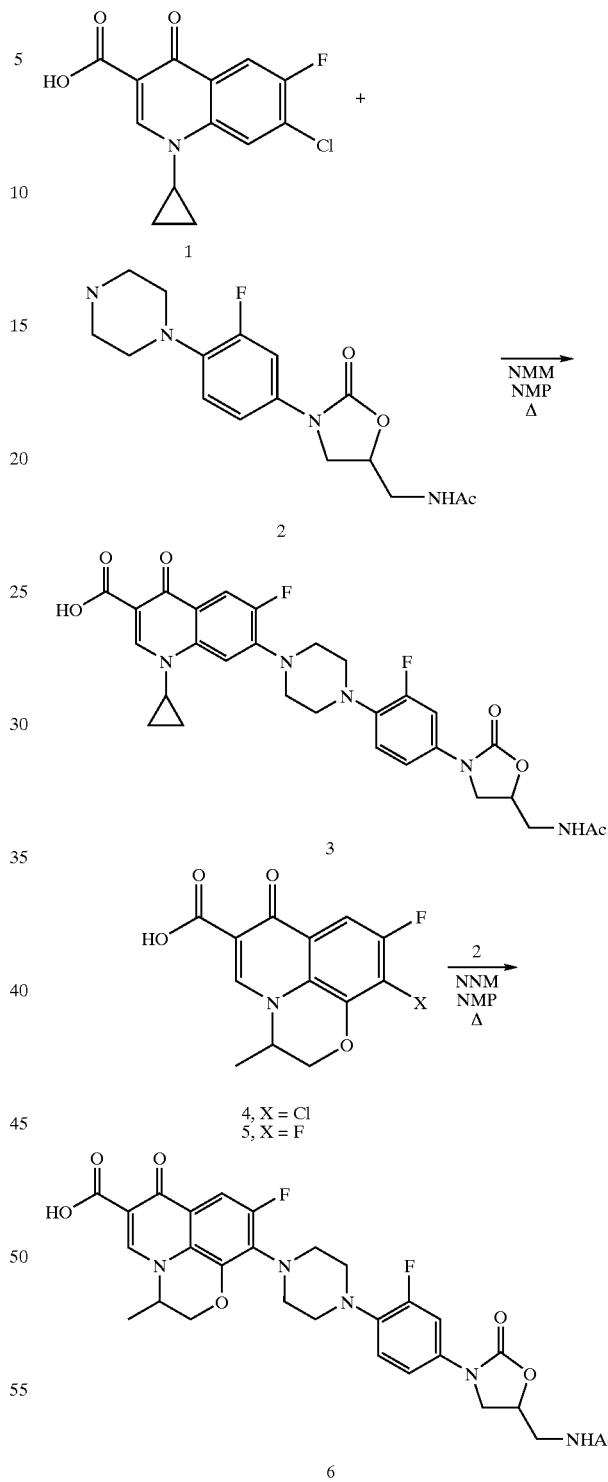

In Scheme 1, an appropriately substituted quinolone, preferably containing a leaving group (LG) at the 7-position (compound A), such as a fluoro, chloro, or triflate derivative, is used as a starting material. Specific examples of such compounds are illustrated by compounds (1), (4), and (5). Compounds (1), (4), and (5) are readily available from a number of commercial sources or, alternatively, are known in the chemical literature or can be readily prepared by one skilled in the art. 7-Chloro-1-cyclopropyl-6-fluoro-4-oxohydroquinoline-3-carboxylic acid (1) is commercially available from Acros Organics, and its synthesis is described in German Patents DE 3142854, DE 3248505, and DE 3248507. 1-Cyclopropyl-6,7-difluoro-4-oxo-3-quinolinecarboxylic acid is commercially available from Louston International, and its synthesis is described in German patent DE3248507. 9,10-Difluoro-3-methyl-7-oxo-2,3-dihydro-7H-[1,4]oxazino[2,3,4-λ]quinoline-6-carboxylic acid is commercially available from Maybridge Chemical Company and its synthesis is described in Japanese patents JP 57088182 and JP 58072589 and EP 47005. 9-Chloro-10-fluoro-3-methyl-7-oxo-2,3-dihydro-7H-[1,4]oxazino[2,3,4-λ]quinoline-6-carboxylic acid is commercially available from Commercially available from Zhejiang Hengdian Imp. & Exp. Co., Ltd. and its synthesis is described in Chem. Pharm. Bull., 32, 4907–13 (1984) and EP 206283.

In one embodiment, the appropriately substituted quinolone (1), (4), or (5) is treated with an oxazolidinone, isoxazoline, or isoxazolinone substituted with an sufficiently nucleophilic linking group, L, such that the subsequent nucleophilic substitution reaction provides, in a one-pot reaction sequence, the respective crude oxazolidinone-, isoxazoline-, or isoxazolinone-substituted quinolone (I).

The L group on the oxazolidinone, isoxazoline, or isoxazolinone can be introduced by standard synthetic methods from commercially available reagents as described hereafter. For example, when quinolone (1), (4), or (5) is treated with 5-(S)-aminomethyl-3-(3-fluoro-4-piperazinophenyl)oxazolidine-2-one in N-methylpyrroline-2-one (NMP) and N-methylmorpholine (NMM), the respective crude oxazolidinone-substituted quinolone (3) or (6) is formed in moderate to high yield. Compounds (3) and (6) then can be purified following chromatographic techniques well known in the art.

Alternately, Scheme 3 outlines a representative procedure for preparing compounds where a carbon-carbon bond connects the quinolone fragment to a phenyloxazolidinone subunit. Quinolone triflates 7a,b, (Kiely et. al. *J.*

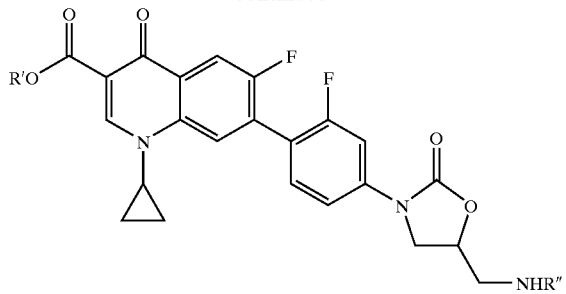

9a, R' = Bn R" = BOC
9b, R' = Et, R" = BOC
10a, R' = Bn, R" = Ac
10b, R' = Et, R" = Ac
11, R' = H, R" = Ac

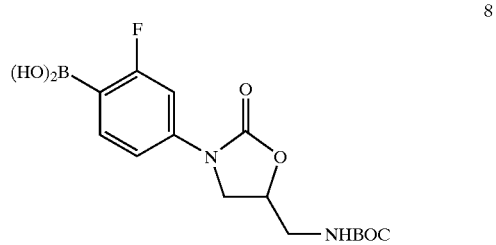

8

*Heterocyclic Chem.* 1991, 28, 1581–1585), is reacted with boronic acid 8 in the presence of 1,2-dimethoxyethane, aqueous dibasic potassium phosphate and a suitable palladium catalyst, such as bis(triphenylphosphine)palladium bichloride or tetrakis(triphenylphosphine)palladium, and at a suitable temperature, preferably at reflux, to generate the respective coupled products 9a,b. It will be apparent to one skilled in the art that compounds 9a,b are both antimicrobial compounds and synthetic intermediates. For example, the tert-butoxycarbonyl (BOC) moiety of 9a,b can be removed with, for example, trifluoroacetic acid to give an amino intermediate which can be further elaborated, for example, acylated, employing conditions described below. Additionally, the ester moiety of 10 or a subsequent acylated derivative can be hydrolyzed under acidic or basic conditions to give the corresponding carboxylic acid 11. Furthermore, when R¹=Bn hydrogenolysis in the presence of a suitable catalyst such as palladium on carbon also affords the corresponding carboxylic acid 11.

As shown in Scheme 4 below, the synthetic procedures leading to isoxazoline- and isoxazolinone-substituted quinolones of the present invention closely parallel the above procedure.

Scheme 3

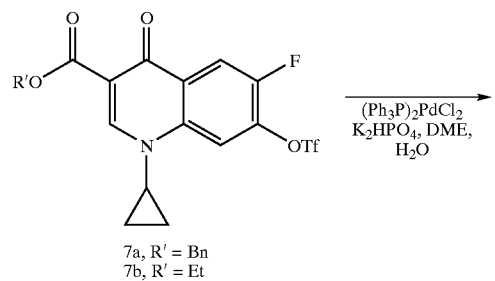

7a, R' = Bn
7b, R' = Et

Scheme 4

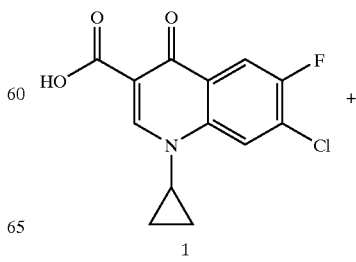

1

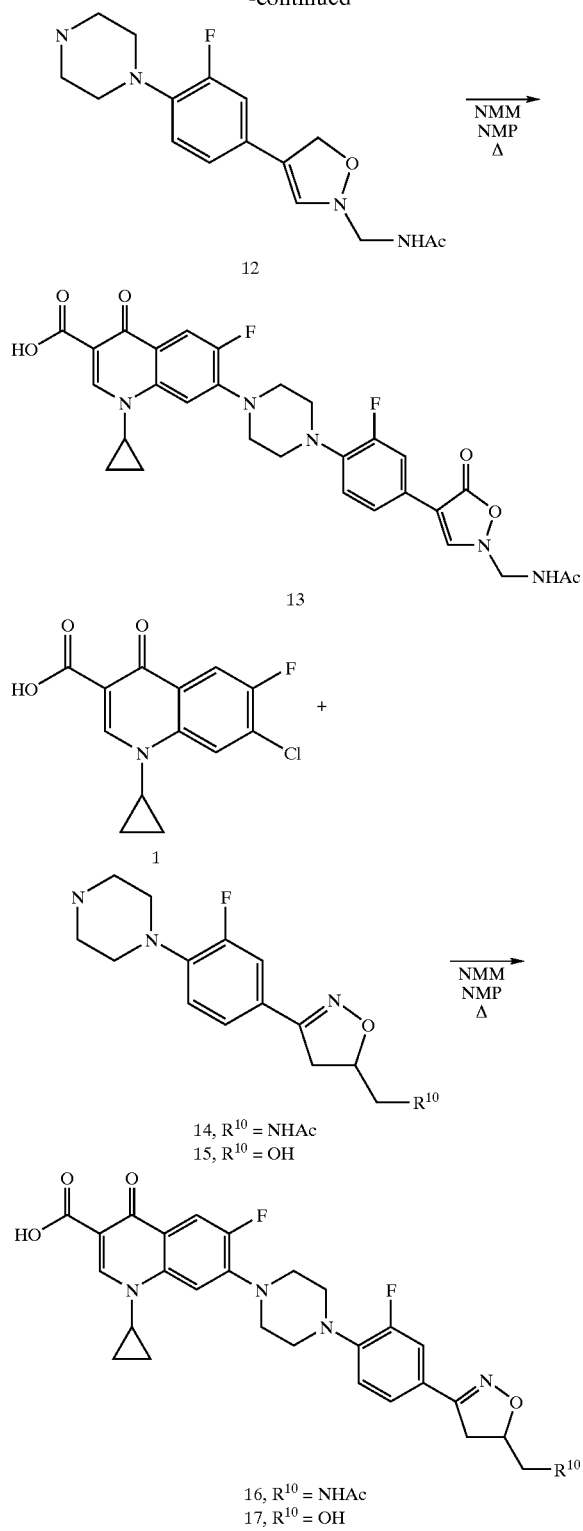

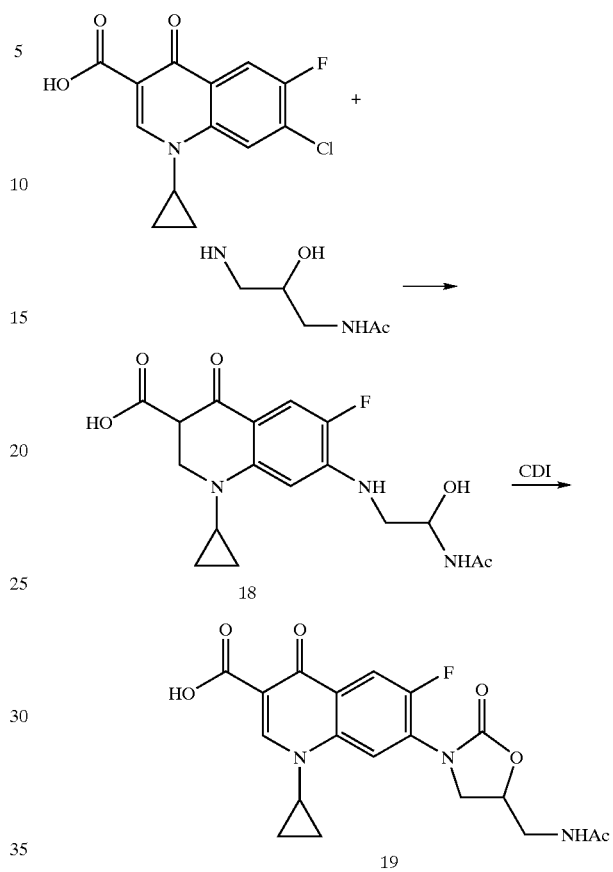

In another embodiment, the linking group between the oxazolidinone, isoxazoline, or isoxazolinone ring and the quinolone ring of the quinolone compounds (Scheme 1) of the present invention is a bond. In these cases, the oxazolidinone, isoxazoline, and isoxazolinone is formed subsequent to the nucleophilic substitution reaction. This is illustrated in Scheme 5.

For example, quinolone (1) is treated with 1-acetyl-3-amino-2-(S)-oxypropylamine in NMP and NMM, as described above, to form an aminoalcohol intermediate (18). The aminoalcohol intermediate (18) then is converted, in a one-pot reaction sequence, to a crude oxazolidinone-substituted quinolone (19) by treatment with carbonyldiimidazole (CDI). Conversion of amino alcohols to oxazolidinones is achieved by known process as (See e.g., *J. Med. Chem.*, 32, 1673 (1989).).

In another embodiment, the oxazolidinone-, isoxazoline-, and isoxazolinone-substituent is covalently bonded to the one-position nitrogen of the quinolone ring system. Scheme 6 illustrates the synthesis of a 1-oxazolidinone-substituted quinolone compound of the present invention.

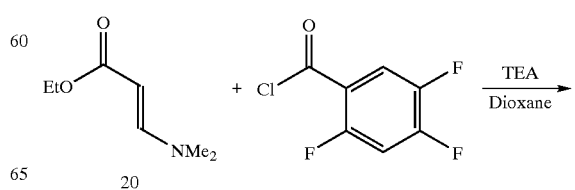

-continued

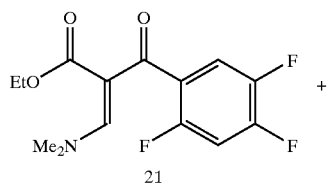
21

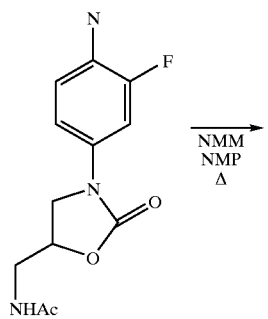

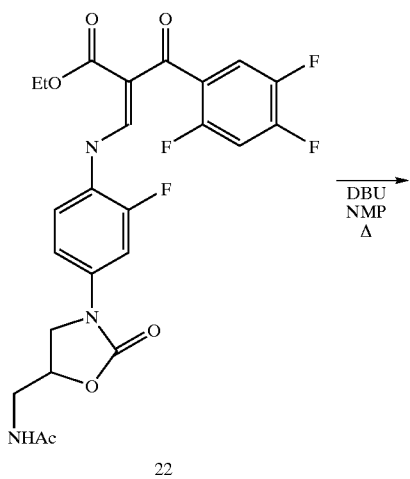
22

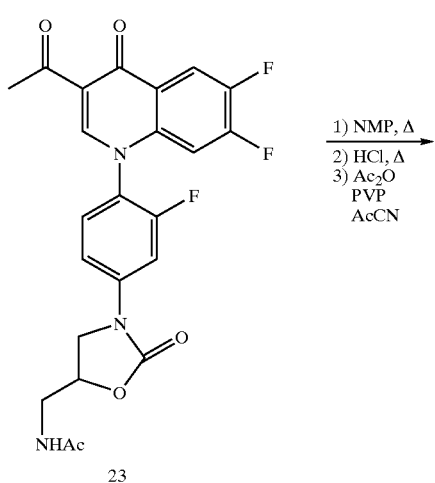
23

-continued

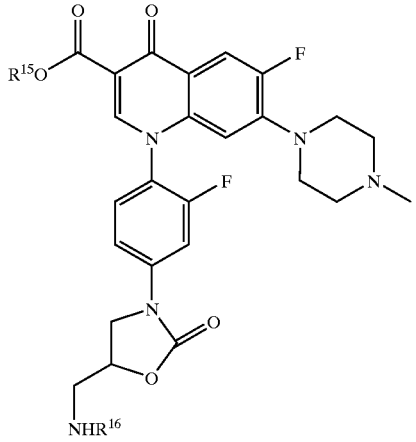

24, R$^{15}$ = Et, R$^{16}$ = Ac
25, R$^{15, 16}$ = H
26, R$^{15}$ = H, R$^{16}$ = Ac

Briefly, ethyl 3-dimethylaminoacrylate (20) is converted to ethyl 2-(dimethylamino)methylene-2-(2,4,5-trifluorobenzoyl)acetate (21) in the presence of 2,4,5-trifluorobenzoyl chloride, triethylamine, and 1,4-dioxane. Reaction of compound (21) with 5-(S)-acetamidomethyl-3-(4-amino-3-fluorophenyl)-oxazolidine-2-one provides compound (22), which then is heated in the presence of diazabicyclo[4.4.0]undec-2-ene (DBU) and an excess of NMP to facilitate cyclization to quinolone-oxazolidinone (23). Quinolone-oxazolidinone (23) can be converted directly to the corresponding N-methylpiperazinyl compound (24) by treatment with 1-methylpiperazine in the presence of NMP. Hydrolysis of compound (24) in the presence of aqueous hydrogen chloride yields acid amine (25). Acylation of amine (25) provides a oxazolidinone-substituted quinolone (26) of the present invention. The synthetic procedures which provide the N$^1$-isoxazoline- and isoxazolinone-substituted quinolones of the present invention closely parallel the above procedure.

Isoxazoline- and isoxazolinone intermediates (12), (14), and (15) can be obtained a variety of syntheses. The preferred routes are depicted in Schemes 7 and 8, respectively. It will be apparent to those skilled in the art that the following are representative examples, and that modifications of the disclosed synthetic protocols allow for the preparation of isoxazoline- and isoxazolinone intermediates.

Scheme 7

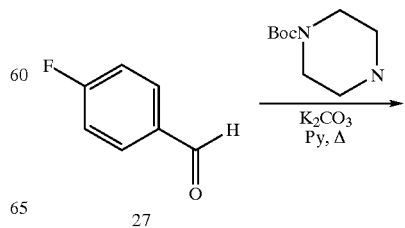
27

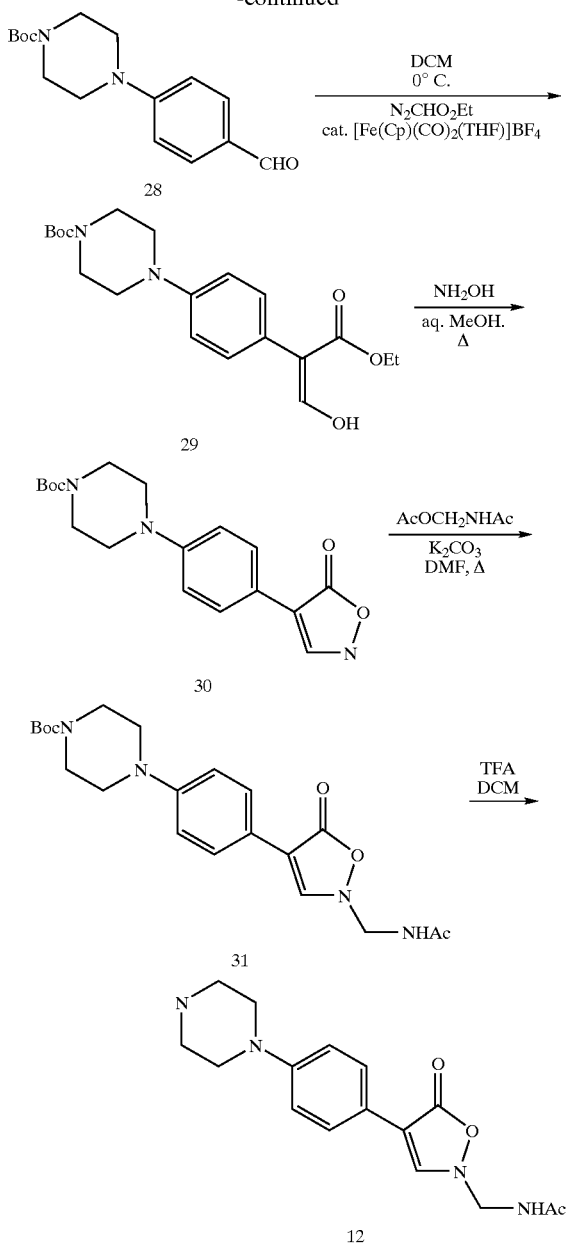

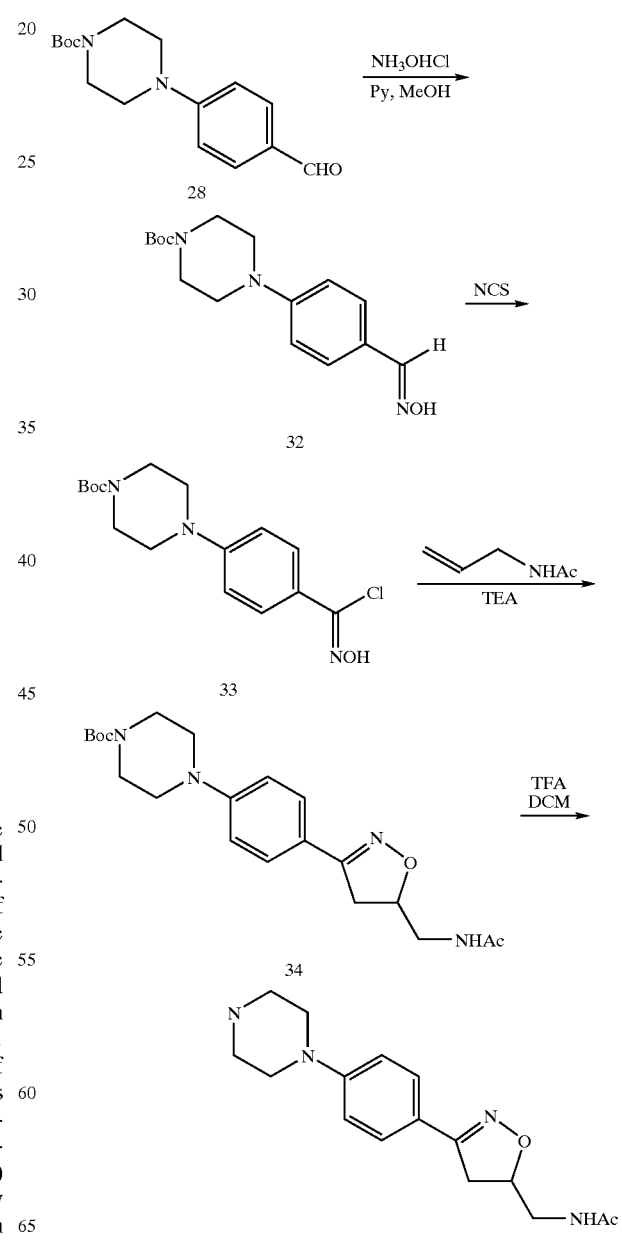

As shown in Scheme 8, intermediate (28) also can be reacted with hydroxylamine hydrochloride in a polar protic solvent, such as methanol (MeOH), in the presence of a base, such as pyridine, to afford oxime (32). The oxime (32) then is oxidized by N-chlorosuccinamide (NCS) in an appropriate solvent, such as dichloromethane, to give the oximyl chloride (33). Alternatively, oximyl chloride (33) can be formed in situ and directly treated with an allylic compound such as N-acetylallylamine or allyl alcohol, in the presence of a suitable-solvent, such as dichloromethane (DCM), to give compounds (34) and (35), respectively. The BOC protecting group then is removed by reaction with an acid, preferably trifluoroacetic acid in dichloromethane, to furnish piperazinylarylisoxazolinone compounds (14) and (15), respectively.

As shown in Scheme 7, p-fluorobenzaldehyde (27) can be reacted with commercially available BOC-protected piperazine, 1-(t-butoxycarbonyl)piperazine (Aldrich Chemical Company, Inc., Milwaukee, Wis.), in the presence of potassium carbonate and a suitable solvent, such as pyridine (Py), and at a suitable temperature (e.g., reflux) to provide piperazinyl intermediate (28). The formation of ester alcohol (29) results from the condensation of Compound (2–8) with ethyl diazoacetate, as described in Mahmood et al., *J. Org. Chem.*, 63, pgs. 3333–3336 (1998). Addition of hydroxylamine, followed by warming to reflux in aqueous methanol, yields piperazinylarylisoxazolinone (30). Compound (30) then is converted to the corresponding methylacetamide (31) by reaction with N-(hydroxymethyl) acetamide acetate/DMF. The BOC group then is removed by treatment with an acid, preferably trifluoroacetic acid in dichloromethane (DCM), to yield piperazinylarylisoxazolinone Compound (12).

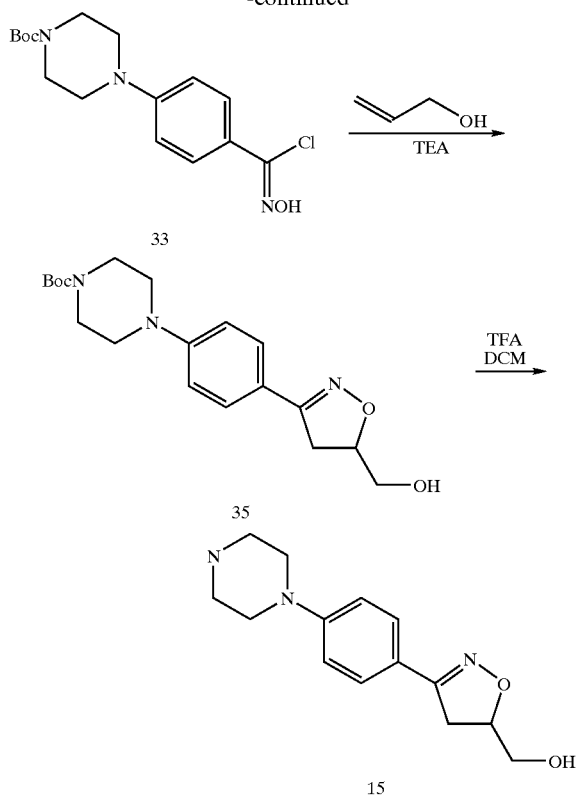

Other combinations of a quinolone with an oxazolidinone, an isoxazolinone, or an isoxazoline, also are possible. One embodiment involves covalent binding of the oxazolidinone, isoxazolinone, or isoxazoline to the side chains of the preferred C-7 quinolone substituents, for example the side chain amino group of optically active (amino) cycloalkylamino C-7 substituents.

The oxazolidinone- and isoxazoline-substituted quinolones (I) of the present invention contain at least one chiral center. It is apparent to one skilled in the art that when one chiral center is present, the compound can exist as one of two possible optical isomers ((R) and (S) enatiomers) or a racemic mixture of both. Both individual (R) and (S) enatiomers, as well as mixtures thereof, are within the scope of the oxazolidinone- and isoxazoline- substituted quinolones (I) of the invention. In the event a second chiral center is present in the oxazolidinone- and isoxazoline-substituted quinolones (I) of the invention, the resultant diastereomers, in racemic and enantiomerically enriched forms, also are within the scope of the compounds (I) of the invention.

The preferred compounds of the present invention are optically pure enantiomers having the (S)-configuration at $C^5$ of the oxazolidinone or isoxazoline ring, because, for example, S-ofloxacin exhibits a 10 to 100-fold greater potency than R-ofloxacin. However, the racemic mixture also is useful, but a greater amount of the racemic material may be required to produce the same effect as the pure S-enantiomer.

If desired, the mixture of enantiomers is resolved by means known to those skilled in the art. Optically pure material can be obtained by resolution of the racemic mixture by HPLC using a chiral phase, such as a Chiralpack AD column as described in Examples 4 and 6 for compounds 15 and 17 and shown in Scheme 2. Alternatively, resolution of the racemic mixture can be accomplished by selective crystallization of a salt form using methods known to those skilled in the art. See for example, "Optical Remixture Procedures for Chemical Compounds, Vol 1; Amines and Related Compounds," Paul Newman, Optical Remixture Information Center, Manhattan College, Riverdale, N.Y.,10471, 1978. For example, treatment of the R,S-aminomethyl mixture (25) with an appropriate optically active acid, such as (+)-tartaric acid, or alternatively with (−)-tartaric acid, yields a mixture of diastereomeric salts, which can be separated by fractional crystallization to give a salt containing one enantiomer of the racemic mixture. Other suitable optically active acids include (−)-dibenzoyl-tartaric acid, (+)-camphoric acid, (+)- and (−)-malic acid, and (+)-camphor-10-sulfonic acid. By reacting the diastereomeric salt with a base, the optically pure free amino compound (25) is obtained.

A compound of formula (I), or a prodrug or a physiologically acceptable salt or solvate thereof, can be administered as the neat compound or as a pharmaceutical composition containing either entity.

The pharmaceutical compositions of the present invention can be prepared by admixing a compound of formula (I) with a solid or liquid pharmaceutically acceptable carrier, and, optionally, with pharmaceutically acceptable adjuvants and excipients employing standard and conventional techniques. Solid form compositions include powders, tablets, dispersible granules, capsules, cachets and suppositories. A solid carrier can be at least one substance which also can function as a diluent, flavoring agent, solubilizer, lubricant, suspending agent, binder, tablet disintegrating agent, and encapsulating agent. Inert solid carriers include magnesium carbonate, magnesium stearate, talc, sugar', lactose, pectin, dextrin, starch, gelatin, cellulosic materials, a low melting wax, cocoa butter, and the like. Liquid form compositions include solutions, suspensions, and emulsions. For example, compounds of the present invention can be dissolved in water, water-propylene glycol, or water-polyethylene glycol, optionally containing suitable conventional coloring agents, flavoring agents, stabilizers and thickening agents. The oxazolidinone-, isoxazoline-, and isoxazolinone-substituted quinolones (I) can be used alone, or in conjunction with other antibacterial agents and/or non-antibacterial agents, as known to those skilled in the art.

Pharmaceutically acceptable refers to those properties and/or substances which are acceptable from a pharmacological or toxicological point of view and from a physical or chemical point of view regarding composition, formulation, stability, patient acceptance, and bioavailability. Pharmaceutically acceptable hydrate means hydrates useful for administering the compounds of this invention, and suitable hydrates include the compounds complexed with at least one water molecule.

Pharmaceutically acceptable salts means salts useful for administering compounds of the present invention. Suitable salts include acid addition salts when a basic group is present, such as occurs with the preferred piperazinyl group. Acid addition salts include those made from mineral adds, for example, hydrochloric, hydrobromic, hydroiodic, sulfuric, phosphoric, and the like, organic sulfonic acids, e.g., methanesulfonic, 2-hydroxyethyl sulfonates, organic carboxylic acids, e.g., amino and carbohydrate acids, e.g., gluconic, galacturonic, acetates, propionates, lactates, maleates, malates, succinates, tartrates, citric acid, fumarates, and the like. These salts can be in a hydrated form.

Pharmaceutically acceptable prodrugs means prodrugs useful for administering the compounds of this invention.

Suitable prodrugs include acid derivatives, for example, amides, esters, for example, methyl esters, ethyl esters, and the like. It also is appreciated by those skilled in the art that the appropriate N-oxides of the nitrogens of the oxazolidinone-, isoxazoline-, and isoxazolinone-substituted quinolones (I) are included within the scope of the invention. These prodrugs also can be in a hydrated form.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the does lethal to 50% of the population) and the $ED_{50}$ (the dose lethal to 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

Humans and other mammals, for example, cattle, horses, sheep, hogs, dogs, and cats, can be treated with the oxazolidinone-, isoxazoline-, and isoxazolinone-substituted quinolones (I) of the present invention. The quinolones (I) of the present invention can be administered in a manner and in dosage forms similar to those of the known anti-bacterial agents described above. In therapeutic use for treating, or combating, bacterial infections in humans and warm-blooded animals, the compounds of formula (I), or pharmaceutical compositions thereof, are administered by conventional techniques, such as orally in solid and liquid dosage forms and/or parenterally (IV, IM, SQ), at a unit dosage form to obtain and maintain a concentration, that is, an amount, or blood-level of active component in the animal undergoing treatment which is antibacterially effective or appropriate.

Generally, the amount of compound (I) in a pharmaceutical composition is about 0.5% to about 90% by weight. An antibacterially effective dosage of compound (I) is about 0.1 to about 100 mg/kg of body weight/day, more preferably about 3 to about 50 mg/kg of body weight/day. The quantity of the oxazolidinone-, isoxazoline-, and isoxazolinone-substituted quinolone compounds of formula (I) in the pharmaceutical composition, the exact unit dosage form thereof to be administered, the frequency of administration, and the route of administration will vary, and can be adjusted widely depending upon a number of factors known to those skilled in the art including the particular mode of administration, the particular compound being used, the potency of the particular compound, the desired concentration, the age, weight, sex, and general physical condition and requirements of the patient, the nature and severity of the bacterial infection being treated, and the like, as is well known to the physician treating infectious diseases. Also, it is to be understood that the initial dosage administered can be increased beyond the above upper level in order to rapidly achieve the desired blood-level or the initial dosage can be smaller than the optimum and the daily dosage can be progressively increased during the course of treatment depending on the particular situation. The usual pharmaceutical dosage forms appropriate for parenteral (mixture, suspension in oil) and oral (tablet, capsule, syrup, suspension, etc) administration are known to those skilled in the art.

Compounds of the present invention can be administered by any suitable route, for example by oral, topical, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

If the compounds or pharmaceutical compositions of the present invention are administered parenterally, i.e., by injection, for example, by intravenous injection or by other parenteral routes of administration, it generally is as a soluble salt (acid addition salt or base salt) of the compound according to formula (I) in a pharmaceutically acceptable amount dissolved in a pharmaceutically acceptable liquid carrier such as, for example, water-for-injection, and a buffer to provide a suitable buffered isotonic solution, for example, having a pH of about 3.5 to about 6.

Suitable-buffering agents include, for example, trisodium orthophosphate, sodium bicarbonate, sodium citrate, N-methylglucamine, L(+)-lysine, and L(+)-arginine. A compound of formula (I) generally is dissolved in the carrier in an amount sufficient to provide a pharmaceutically acceptable injectable concentration in the range of about 1 to about 400 mg/ml of solution. The resulting liquid pharmaceutical composition is administered so as to obtain the above-mentioned antibacterially effective amount of dosage.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5 to about 95% compound of the present invention, and preferably from about 25 to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5 to about 90% by weight of a compound of the present invention, and preferably about 1 to about 50% of a compound of the present invention.

When a therapeutically effective amount of a compound of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, and isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention can be delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

For topical administration, the present compounds can be applied in neat form, e.g., when the compound is a liquid. However, it is desirable to administer the compounds to the skin as compositions in combination with a dermatologically acceptable carrier, which can be a solid, semi-solid, or a liquid. Useful solid carriers include, but are not limited to, finely divided solids such as talc, clay, microcrystalline cellulose, silica, alumina, and the like. Useful liquid carriers include, but are not limited to, water, alcohols, glycols, and water-alcohol/glycol blends in which the present compounds can be dissolved or dispersed at effective levels, optionally with the aid of a surfactant. Adjuvants, such as fragrances and additional antimicrobial agents, can be added to optimize the properties for a given use. The resultant liquid compositions can be applied topically by absorbent pads, used to impregnate bandages and other dressings, or sprayed onto the affected area using pump-type or aerosol sprayers.

For veterinary use, a compound of formula (I) or a nontoxic sale thereof, is administered as a suitably acceptable formulation in accordance with normal veterinary practice. The veterinarian can readily determine the dosing regimen and route of administration that is most appropriate for a particular animal.

General Methods and Definitions

Reagents were purchased from commercial sources and used without further purification. All temperatures are in degrees Centigrade. When solvent pairs are used, the ratios of solvents used are volume/volume (v/v). When the solubility of a solid in a solvent is used the ratio of the solid to the solvent is weight/volume (wt/v). Reactions with moisture-sensitive reagents were performed under a nitrogen atmosphere. Concentration of solutions was performed by reduced pressure rotary evaporation. Brine refers to an aqueous saturated sodium chloride mixture. High performance liquid chromatography (HPLC) analysis and purification were performed using Beckman System Gold®; detection at 220 nm. Analytical HPLC was performed on a YMC 5 micron C18 (4.6 mm×50 mm) reverse phase (RP) column (gradient from 100% of the aq. 0.1% trifluoroacetic acid (TFA) to 100% of 0.1% TFA in acetonitrile (MeCN) over 6 min, flow rate 2.0 mL/min). Preparative thin-layer chromatography (TLC) were performed using EM silica gel (SG) 60 $F_{254}$ plates (20×20 cm, thickness 2 mm). NMR refers to nuclear magnetic resonance spectroscopy. $^1$H NMR refers to proton nuclear magnetic resonance spectroscopy with chemical shifts reported in ppm downfield from tetramethylsilane. Mass-spectra (MS) refers to mass spectrometry expressed as m/e or mass/charge unit and was obtained using electron impact (EI) technique. $[M+H]^+$ refers to the positive ion of a parent plus a hydrogen atom. Retention time ($R_t$) is in minutes and refers to x. IR refers to infrared spectroscopy. FTIR refers to Fourier Transform IR.

In the following examples, the following abbreviations are used: millimole (mmol), milliliter (mL), potassium carbonate ($K_2CO_3$), ethyl acetate (EtOAc), DMSO (dimethyl sulfoxide), magnesium sulfate ($MgSO_4$), sodium bicarbonate ($NaHCO_3$), and ethyl alcohol (EtOH).

EXAMPLES

The following examples describe how to prepare the various compounds and/or perform the various processes of the invention, and are to be construed as merely illustrative, and not limitations of the preceding disclosure in any way whatsoever. Those skilled in the art will recognize appropriate variations from the procedures both as to reagents and as to reaction conditions and techniques.

General Procedure for the Synthesis of Quinolone-7-yl Linked Quinolone-Oxazolidinones and Related Analogs A mixture of an appropriate nucleophile linked oxazolidinone, or an oxazolidinone precursor such as an amino alcohol, (1–2 mmol) with an appropriate 7-substituted quinolone (preferably, 7-fluoro, 7-chloro, or 7-triflate derivative) (1 mmol) in N-methylpyrrolidine-2-one (NMP) (2 mL), N-methylmorpholine (NMM) (0.4 mL) and (optionally, DMSO, as an additional co-solvent, is stirred at 110–130° C. for 24–96 h (preferably, 24–48 h (hours) and 96 h for reactions with 7-fluoro and 7-chloroquinolones, respectively). The mixture is cooled to room temperature (r.t.), and a majority of the solvent removed under vacuum. The residue is triturated with water (7 mL), precipitated, filtered, washed with excess water, THF (ca. 4×15 mL), ether, and dried under vacuum. Optionally, the resulting intermediate amino alcohol derivative is purified by crystallization from an appropriate solvent (e.g., MeOH) or by silica gel column chromatography (eluent: dichloromethane-MeOH). The amino alcohol (1 mmol) is dissolved in a aprotic organic solvent (e.g., tetrahydrofuran (THF) or NMP) (2–5 mL), and carbonyldiimidazole (1.1 mmol) is added. Optionally, an organic base is added (e.g., imidazole) (1.1 mmol). The mixture is stirred at 20–40° C. for 1–3 h. The solvent is removed under vacuum, and the crude product is purified by crystallization from an appropriate solvent (e.g., MeOH) or by silica gel column chromatography (eluent: dichloromethane-MeOH). Optionally, the carboxylic functionality is esterified under standard alcohol coupling conditions (e.g., polyethyleneglycol with diethyl cyanophosphate, 4-dimethylaminopyridine in NMP at 20–40° C. for 4–8 h) to provide an ester prodrug derivative.

Example 1

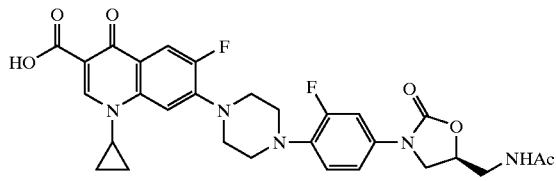

Preparation of 7-[4-[(5-(S)-Acetamidomethyloxazolidine-2-one-3-yl)-2-fluorophenyl]piperazine-1-yl]-3-carboxy-1-cyclopropyl--6-fluoro-1,4-dihydroquinoline-4-one (Compound 3)

Compound 3 was prepared from 5-(S)-aminomethyl-3-(3-fluoro-4-piperazinophenyl)oxazolidine-2-one (0.372 g, 1.1 mmol) and 3-carboxy-1-cyclopropyl-7-chloro-6-fluoro-1,4-dihydroquinoline-4-one (0.282 g, 1 mmol) according to the General Procedure for the Synthesis of Quinolone-7-yl Linked Oxazolidinones. The reaction was performed at 120° C. for 96 h. Yield 0.36 g (62%). MS(m/z): 582 [M+H]$^+$. R$_t$ 4.6 min.

Example 2

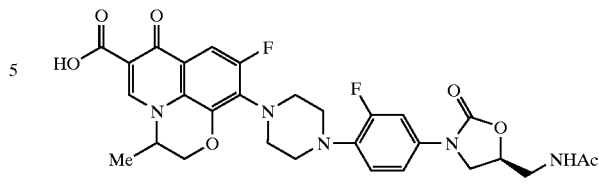

Preparation of 10-[4-[(5-(S)-Acetamidomethyloxazolidine-2-one-3-yl)-2-fluorophenyl]piperazine-1-yl]-6-carboxy-9-fluoro-2,3-dihydro-3-methyl-7-oxo-7H-pyrido[1,2,3-de]-1,4-benzoxazine (Compound 6)

Compound 6 was prepared from 5-(S)-aminomethyl-3-(3-fluoro-4-piperazinophenyl)oxazolidine-2-one (0.372 g, 1.1 mmol) and 9.10-difluoro-2,3-dihydro-3-methyl-7-oxo-7H-pyrido[1,2,3-de]-1,4-benzoxazine-6-carboxylic acid (0.281 g, 1 mmol) according to the General Procedure for the Synthesis of Quinolone-7-yl Linked Oxazolidinones. The reaction was performed at 110° C. for 24 h. Yield 0.444 g (74%). MS (m/z): 598 [M+H]$^+$. R$_t$ 4.5 min. The separation of enantiomers by chiral HPLC provides the preferred (S)-configuration isomer.

Example 3

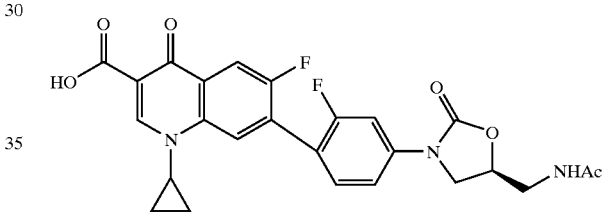

Preparation of 7-(4{(5S)-5-[(Acetylamino)methyl]2-oxo-1,3-oxazolidin-3-yl}-2-fluorophenyl)-1-cyclopropyl-6-fluoro-4-oxo-1,4-dihydro-3-quinolinecarboxylic acid (Compound 11)

Benzyl-1-cyclopropyl-6-fluoro-4-oxo-7-{[(trifluoromethyl)sulfonyl]oxy}-1,4-dihydro-3-quinolinecarboxylate (Compound 7a)

A slurry of 1-cyclopropyl-6-fluoro-4-oxo-7-hydroxy-1,4-dihydro-3-quinolinecarboxylate (1.51 g, 5.75 moles), prepared as described in Kiely, J. S.; Laborde, E,; Lesheshki, L. E.; Busch, R. A. *J. Heterocyclic Chem.* 1991, 28, 1581–1585, in dry pyridine (15 mL) was cooled to 0E C and treated via syringe with trifluoromethanesulfonic anhydride (2.5 mL, 14.86 moles). The resulting homogeneous, amber-colored solution was warmed slowly to room temperature and stirred for 24 hours. Benzyl alcohol (20 mL, 193.3 moles) was added, and the reaction stirred at room temperature for 2 hours. After pouring the solution into 100 mL of water, the aqueous phase was extracted (3×) with CH$_2$Cl$_2$. The combined organic layers were dried (Na$_2$SO$_4$), filtered and evaporated. The crude product was chromatographed on a Biotage 40 g column. The column was conditioned and loaded with CH$_2$Cl$_2$ and eluted with 850 mL of CH$_2$Cl$_2$ and 800 mL of 5% MeOH/CH$_2$Cl$_2$. Fractions 7–13 (A) and fractions 27–28 (B) (~45 mL cuts) were combined and evaporated, but neither was pure. Impure fraction A contained benzyl alcohol, which was removed in a nitrogen stream. The resulting solids were triturated with EtOAc, filtered and dried (House vacuum, 55EC, 1 hour) to yield Compound 7a as a white solid (36A) that weighed 99.0 mg (3.5%). Another 67 mg of 7a was obtained from the filtrate. Impure fraction B was recrystallized from MeOH//CH$_2$Cl$_2$ and EtOAc. The solids (36B) were collected by suction filtration and dried (house vacuum, 55EC, 1 hour) to afford Compound 7a as an off-white solid that weighed 285 mg (10%). Another 235 mg of Compound 7a was obtained in the mother liquors. ES-MS of these products did not provide useful information. $^1$H NMR (DMS)-d$_6$, TMS):*8.54 (s, 1 H), 8.30 (d, J=8 Hz, 1 H), 8.04 (d,J=12 Hz, 1 H), 7.49 (m.2 H), 7.42–7.33 (m, 3 H), 5.29 (s, 2 H), 3.69 (m, 1 H), 1.26 (m, 2 H), 1.11 (m,2 H). The $^1$H NMR of 36B was identical to that of 36A. TLC (of 36A and 36B): R$_f$=0.67 (5% EtOAc/MeOH); UV--visualization Preparation of tert-Butyl [(5S)-3-(4-borono-3-fluorophenyl)-2-oxo-1,3-oxazolidin-5-yl] methylcarbamate (Compound 8)

2-Methylpropyl (4-bromo-3-fluorophenyl)carbamate

To a solution of 500 g (4.50 mol) of 3-fluoroaniline and 2 L of CH$_2$Cl$_2$ in a 12 L round bottom flask was added a solution of 473 g (3.42 mol, 0.76 equiv.) of K$_2$CO$_3$ in 2 L of water. Isobutylchloroformate (663 g, 4.86 mol, 1.08 equiv.) was added with stirring via an addition funnel over 3 h so as to allow the isotherm to warm and maintain the mixture at gentle reflux. Gas evolves vigorously near the end of the addition. The organic phase was sampled for GC analysis 1 h after completion of the addition; less than 0.5% 3-fluoroaniline remained. The mixture was quenched by addition of 72 mL of conc. NH$_4$OH. After stirring for 15 minutes, the mixture was neutralized to pH by addition of 120 mL of conc. aq. HCl. The layers were separated, and the aqueous layer was extracted with 1.5 L of CH$_2$Cl$_2$. To the combined organic layers was added 987 g (3.45 mol, 0.77 equiv.) of 1,3-dibromo-5,5-dimethylhydantoin and 2.5 L of water. The mixture was allowed to isotherm to 39E C and held at that temperature by gentle heating for 2 hours. The reaction was judged complete by HPLC analysis of the organic layer. The mixture was cooled to 32E C by addition of 500 g of ice, and the solids not soluble in either liquid layer (mostly hydantoins and partially brominated hydantoins) were removed by filtration. The filtrate layers were separated, extracting the aqueous layer with 500 mL of CH$_2$Cl$_2$. the combined organic layers were added with rapid stirring to a solution of 410 g of Na$_2$SO$_3$ in 3 L of water. The layers were separated, extracting the aqueous layer with 3400 mL of CH$_2$Cl$_2$. The combined organics were distilled on a rotovap and replaced with heptane, maintaining a constant volume. the resulting thick slurry was cooled to 4E over 2.5 h. The solids were collected by filtration, washed with heptane (2×750 mL) and air dried, affording 1097 g (84%) of 2-Methylpropyl (4-bromo-3-fluorophenyl) carbamate as a white crystalline solid.

(5R)-3-(4-bromo--3-fluorophenyl)-5-(hydroxymethyl)-1,3-oxazolidin-2-one

To a solution of 1056 g (3.64 mol) of 2-Methylpropyl (4-bromo-3-fluorophenyl)carbamate in 6.65 L of THF cooled to –15E C in a 22 L round bottom flask was added a solution of 428 g (4.55 mol, 1.25 equiv.) of lithium t-amylate over 10 min via an addition funnel, maintaining –15E to –12E C. In a separate 5 L flask, a solution of 438 g (4.37 mol, 1.20 equiv.) of (S)-3-chloro-1,2-propanediol in 1.75 L of THF was cooled to –25 E C and treated with a 20% t-BuOK solution in THF (2645 mL, 4.29 mol, 1.18 equiv) over 25 min, resulting in a thick but stirrable slurry. This was allowed to warm to 10E over 75 min and then poured into the 22 L flask containing the carbamate solution. The resulting slurry was allowed to warm from 7E to 7E over 1.5 h, monitoring reaction progress by HPLC. Upon completion (~2.5% each of remaining 2-Methylpropyl (4-bromo-3-fluorophenyl)carbamate and the over addition product) a quench solution composed of 1.05 AcOH and 3.5 L of water was added. The layers were separated. The aqueous layer was back-extracted with 1 L of THF, and the combined organic layers were washed with brine. The volatile were removed, giving white solids wet with acetic acid. This material was slurried in 1.6 L of EtOAc. Hexane (4 L) was added over 1 h. The resulting slurry was cooled to 2E over 1 h and filtered, giving 916 g (87%) of (5R)-3-(4-bromo-3-fluorophenyl)-5-(hydroxymethyl)-1,3-oxazolidin-2-one as coarse white crystals: TLC R$_f$=0.008 (50% EtOAc/hexane); HPLC rt=2.55 min; mp 114--121E; [∀]$_D$=+52.2E c=1, MeOH); $^1$H NMR (DMSO)*7.49 (m, 2H), 7.15 (d,1H, J=8.5 Hz), 5.30 (br s, 1H), 4.54 (m,1H), 3.89 (t, 1H, J=8.6 Hz), 3.67 (m, 1H), 3.50 (dd, 1H, J=3.0, 11.8 Hz), 3.39 (dd; 1H, 3.8, 11.8 Hz); $^{13}$C NMR (DMSO)*158.1 (s, J$_{CF}$=241 hz), 154.2 (S), 139.7 (S, J$_{CF}$=10 hz), 133.3 (D), 114.9 (D), 105.9 (d, J$_{CF}$=29 Hz), 100.9 (s, J$_{CF}$=21 Hz); 73.3(d), 61.5(t), 45.9 (t); Anal. calc'd for C$_{10}$H$_9$BrFNO$_3$: C, 41.40; H, 3.13; N, 4.83: Br, 27.55; found: C, 41.11; H, 3.06; N, 4.83: Br, 26.97.

[(5R)-3-(4-bromo-3-fluorophenyl)-2-oxo-1,3-oxazolidin-5-yl]methyl 3-nitrobenzene sulfonate To a slurry of 907 g (3.13 mol) of (5R)-3-(4-bromo--3-fluorophenyl)-5-(hydroxymethyl)-1,3-oxazolidin-2-one in 4.5 L of CH$_2$Cl$_2$ in a 22 L round bottom flask was added 654 mL (4.69 mol, 1.50 equiv.) of triethylamine. The mixture was cooled to 0E C, and a solution of 832 g (34:75 mol, 1.20 equiv) of m-nitrobenzenesulfonyl chloride in 2 L of CH$_2$Cl$_2$ was added, keeping the temperature below 6E C. The mixture was sampled for HPLC, and an additional 55 g of solid m-nitrobenzenesulfonyl chloride was added to drive the reaction to completion. Hydrochloric acid (1M, 4.5 L) was added to the slurry. The solids were collected by filtration and washed with water. The phases in the filtrate were separated, and the aqueous later was extracted with 2×500 mL of CH$_2$Cl$_2$. The combined organic layers were concentrated and combined with the solids previously isolated, 2 L of CH$_2$Cl$_2$ and 2 L of methanol. This slurry was distilled on a rotary evaporator, keeping the volume at ~5 L by adding methanol. The solids were collected by filtration, washed with 1 L of MeOH, and air dried to afford 1415 g (95%) of [(5R)-3-(4-bromo-3-fluorophenyl)-2-oxo-1,3-oxazolidin-5-yl] methyl 3-nitrobenzene sulfonate: TLC R$_f$=0.15 (50% EtOAc hexanes); HPLC rt=5.68 min; mp 153–156E; [∀]$_D$=–76.6E C=1, MeOH/(CH$_2$Cl$_2$)$_;$ $^1$H NMR (DMSO)*8.77 (d, 1H, J=8.2 Hz), 8.71 (s,1H), 8.52 (d, 1H. 7.9 Hz),8.14 (t, 1H, J=8.1 Hz), 7.85 (t, 1H, J=8.5 Hz), 7.73 (dd, 1H, J=2.3, 11.4 Hz), 7.40 (d, 1H, J=8.9 Hz), 5.12 (m, 1H), 4.68 (m, 2H), 4.28 (t, 1H, J=9.4 Hz), 3.89 (m, 1H); $^{13}$C NMR (DMSO)*157.3 (s, J$_{CF}$=242 hz), 152.4 (S), 147.2 (S), 138.3 (S, J$_{CF}$=10 hz), 135.4 (S), 132.7 (D), 132.6 (D), 131.1 (D), 128.2 (D), 121.7 (D) 114.2 (D), 105.3 (D, J$_{CF}$=29 Hz), 100.6 (s, J$_{CF}$=20 Hz), 70.4 (t), 69.0.(d), 44.8 (t); Anal. calc'd for C$_{16}$H$_{12}$BrFN$_2$O$_7$S: C, 40.44; H, 2.55; N, 5.89; Br, 16.81; found: C, 40.22; H, 2.45; N, 5.86; Br, 16.60.

tert-Butyl [(5S)-3-(4-bromo-3-fluorophenyl)-2-oxo-1,3-oxazolidin-5-yl] methylcarbamate In three portions, the sulfonate [(5R)-3-(4-bromo-3-fluorophenyl)-2-oxo-1,3-oxazolidin-5-yl] methyl 3-nitrobenzene sulfonate (1400 g., 2.95 mol) was suspended in 15 mL/g of a solvent mixture of 29% aqueous $NH_4OH$, MeCN, and MeOH in a 5:2.5:1 ratio in an autoclave. The system was sealed and heated to 80E C for 3–4 h with stirring. Upon cooling, the mixtures were extracted three times each with $CH_2Cl_2$. the combined extracts were concentrated, giving the crude amine as solid. The solids were suspended in 8.5 L of $CH_2Cl_2$. Di-t-butyldicarbonate (985 g, 4.42 mol, 1.5 equiv.) was added as a solid over 15 min. with vigorous gas evolution. The mixture was stirred at room temperature overnight, after which the reaction waw complete by TLC. Water (3 L) was added, and stirring was continued for 30 min. The mixture was filtered, washing the solids that collected with additional $CH_2Cl_2$. The layers in the filtrate were separated. The organic layer was concentrated to a white solid, crude tert-butyl [(5S)-3-(4-bromo-3-fluorophenyl)-2-oxo-1,3-oxazolidin-5-yl] methylcarbamate. This was suspended in 3 L of EtOAc and-heated to 70 E C to dissolve. Upon cooling to room temperature, 3 L of hexane was added over 1 h. The resulting slurry was cooled to 1E C. The solids were collected by filtration and washed with hexane to obtain 763 g of tert-butyl [(5S)-3-(4-bromo-3-fluorophenyl)-2-oxo-1,3-oxazolidin-5-yl] methylcarbamate. A second crop was obtained by concentrating the mother liquor to 1.2 L and cooling to 1E C, yielding an additional 50 g (total 813 g, 71%): TLC $R_f$=0.31 (50% EtOac/hexane); HPLC rt=5.02 min; mp 145–146E; [∀]$_D$=+30.0E c=1, MeOH): $^1$H NMR ($CDCl_3$)*7.50 (m, 2H), 7.12 (d, 1H, 8.5 Hz), 5.04 (br s, 1H), 4.77 (m, 1H), 4.01 (t,1H, J=8.7 Hz), 3.84 (m, 1H), 3.53 (m, 2H), 1.40 (S,9H); $^{13}$C NMR ($CDCl_3$) *160.2(s), 157.3 (s, $J_{CF}$=242 Hz), 154.0 (S), 138.8 (s, $J_{CF}$=9 Hz), 133.5 (d), 114.4 (d), 106.8 (d, $J_{CF}$=28 Hz), 103.3 (s, $J_{CF}$=21 Hz), 80.4 (s), 72.1 (d), 47.3 (t), 43.2 (t), 28.2 (q); Anal. calc'd for $C_{15}H_{18}BrFN_2O_4$: C, 46.29; H, 4.66; N, 7.20; Br, 20.53; found: C, 46.32, H, 4.57; N, 7.21, Br, 20.63.

tert-Butyl [(5S)-3-(4-borono-3-fluorophenyl)-2-oxo-1,3-oxazolidin-5-yl] methylcarbamate (Compound 8)

To a solution of 2.00 g (5.14 mmol) of tert-Butyl [(5S)-3-(4-bromo-3-fluorophenyl)-2-oxo-1,3-oxazolidin-5-yl] methylcarbamate in 40 mL of THF was added 1.94 mL (1.49 g, 12.8 mmol, 2.50 equiv.) of N,N,N',N'-tetramethylenediamine. The solution was cooled to –50E, and 4.86 mL (5.45 mmol, 1.06 equiv.) of 1.12 M ethyl magnesium bromide in THF solution was added by syringe. After 5 min., 4.06 mL (10.8 mmol, 2.10 equiv.) of 2.66 M n-butyl lithium in hexane solution was added dropwise by syringe with vigorous stirring, keeping the temperature below 45 EC. A thick slurry resulted, which was stirred for an additional 15 min. Trimethylborate (1.17 mL, 1.07 g, 10.3 mmol, 2.00 equiv.) was added by syringe. The mixture was allowed to warm to 20 EC over 90 min. It was then poured into 25 mL of 4M hydrochloric acid and stirred for 15 min. The layers were separated, and the aqueous layer was extracted with 20 mL of $CH_2Cl_2$ to complete the removal of boronic acid. The combined organic extracts were dried ($MgSO_4$), filtered, and concentrated to give crude Compound 8 as an oil.

Benzyl-7-[4-((5S)-{[(tert-butoxycarbonyl)amino] methyl}-2-oxo-1,3-oxazolidin-3-yl)-2-fluorophenyl]-1-cyclopropyl-6-fluoro-4-oxo-1,4-dihydro-3-quinolinecarboxylate (Compound 9a)

A mixture of Compound 7a (369 mg, 0.76 moles) and Compound 8 (298 mg, 0.84 moles) in 1,2 dimethoxythane (8 mL) was degassed and flushed with nitrogen several times. Dichlorobis(triphenylphosphine)palladium(II) (56.3 mg, 0.08 moles) and 2M $K_2HPO_4$ (0.77 mL, 1.54 moles) was added. The mixture was degassed and flushed with nitrogen several times and then heated at 90EC for 22 hours. After cooling to room temperature, the reaction was concentrated under reduced pressure, and the residue was chromatographed on a Biotage 40 gram column. The column was conditioned with 3:3:4 $CH_2Cl_2$/EtOAc/heptane, loaded with $CH_2Cl_2$ and eluted with 900 mL of 3:3:4 $CH_2Cl_2$/EtOAc/heptane and 500 mL of EtOAc. Fractions 23–49 (~20 mL cuts) were combined, evaporated and dried (high vacuum, r.t., 1 hour) to yield 257.1 mg (52%) of Compound 9a as a tan, amorphous solid. MS (ESI+) for $C_{35}H_{33}F_2N_3O_7$ m/z 646.3 (M+H)$^+$. $^1$H NMR ($CDCl_3$, TMS); 8.64(S, 1 h), 8.24 (D, J=13 Hz, 1 h), 7.98 (D, J=7 hz, 1 H), 7.71–7.61 (m,2 H), 7.55–7.47 (m, 3 H), 7.42–7.33 (m, 3 H), 5.42 (s, 2 H.), 5.03 (m, 1 H), 4.82 (m, 1 H), 4.11 (m, 1 H), 3.94 (m, 1 H), 3.57 (m,2 H), 3.49 (m, 1 H), 1.43 (s, 9 H), 1.33 (m,2 H), 1.16 (m,2 H). TLC: $R_f$=0.14 (80% EtOAc/hexane); UV-visualized.

Benzyl-7-(4-{(5S)-5-{(acetylamino)methyl}-2-oxo-1,3-oxazolidin-3-yl}-2-fluorophenyl)-1-cyclopropyl-6-fluoro-4-oxo-1,4-dihydro-3-quinolinecarboxylate (Compound 10a)

A solution of Compound 9a (253 mg, 0.391 moles) in 5.2 mL of $CH_2Cl_2$ at 0EC was treated via syringe with trifluoroacetic acid (2.6 mL, 33.7 moles). The resulting solution was stirred at 0EC for 30 minutes and at room temperature for 1.5 hours. After concentrating the reaction under reduced pressure, the residue was dried (high vacuum, r.t., 2 hours) to afford the trifluoroacetic acid salt as an amber, amorphous solid (372 mg, over theory). The above salt was dissolved in 6.5 mL of pyridine-at room temperature and treated with acetic anhydride (1.5 mL, 15.9 moles). After stirring at room temperature for 17 hours, the reaction was cooled to 0EC and quenched with 1.5 mL of MeOH. The reaction was stirred at 0EC for 10 minutes and at room temperature for 20 minutes. Solvent was removed under reduced pressure, and the crude product (863 mg) was chromatographed on a Biotage 40 gram column. The column was conditioned with EtOAc, loaded with EtOAc (plus a small amount of $CH_2Cl_2$) and eluted with 500 mL of EtOAc, 500 mL of 2% MeOH/ $CH_2Cl_2$ and 500 ml of 5% MeOH/$CH_2Cl_2$. Slightly impure fractions 42–70 (~20 mL cuts) were combined, evaporated (271 mg) and chromatographed again on a Biotage 8 gram column. The column was conditioned, loaded and eluted with 5% MeOH/$CH_2Cl_2$. Fractions 7–44 (about 7 mL cuts) were combined, evaporated and dried (house vacuum, r.t., 16 hours) to generate 218.5 mg (95%) of Compound 10a as a beige solid. MS (ESI+) for $C_{32}H_{27}F_2N_3O_6$ m/z 588.2 (M+H)$^+$. $^1$H NMR ($CDCl_3$, +2 drops $CD_3OD$, TMS):*8.70 (s, 1 H), 8.17 (d, J=10 Hz, 1 H), 8.03 (m,1 H), 7.60 (in, 1 H), 7.50–7.46 (m,3 H), 7.41–7.31 (m, 4 H), 5.41 (s, 2 H), 4.83 (m, 1 H), 4.11 (t, J=9 Hz, 1 H), 3.86 (m, 1 H), 3.66 (m, 2 H), 3.54 (m, 1 H), 2.03 (s, 3 H), 1.36 (m, 2 H), 1.18 (m, 2 H). TLC: $R_f$=0.28 (5% MeOH/$CH_2Cl_2$); UV-visualized 7-(4-{(5S)-5-[(Acetyl amino)methyl]-2-oxo-1,3-oxazolidin-3-yl}-2-fluorophenyl)-1-cyclopropyl-6-fluoro-4-oxo-1,4-dihydro-3-quinolinecarboxylic acid (Compound 11)

A solution of Compound 10a (215 mg, 0.365 moles) in absolute ethanol was treated with 30 mg of 10% Pd/C. The mixture was placed on the hydrogenator at room temperature at 40 psi $H_2$ for 3 hours. Since TLC analysis indicated the presence of starting material, an additional 30 mg of catalyst was added, and the reaction was returned to the hydrogenator at 40 psi of $H_2$ for 16 hours. After removing the catalyst by filtration through a pad of Elite and washing the filter cake with absolute ethanol, the filtrates were combined and concentrated leaving a yellowish-black residue (160 mg). The residue was chromatographed on a Biotage 8 g column. The column was conditioned, loaded and eluted with 5% MeOH/$CH_2Cl_2$, but only mixed fractions were obtained. Fractions containing the desired product were combined and concentrated leaving a solid that was crystallized from EtOAc/heptane. TLC analysis of the solids (22 mg) revealed that crystallization did not upgrade the product. Therefore, the solids and mother liquors were dissolved n a minimal amount of MeOH/$CH_2Cl_2$ and loaded onto two 500 m prep TLC plates. After eluting once with 5% MeOH/$CH_2Cl_2$, the plates were eluted a second time with 5% MeOH/$CH_2Cl_2$+0.5% HOAc. Separation was not perfect, but a clean sample of the desired band was isolated affording 21.8 mg (12%) of Compound 11 as a gold solid. This product decomposed at 120EC. MS (ESI+) for $C_{25}H_{21}F_2N_3$)6 m/z 498.2 $(M+H)^+$. High resolution MS (FAB): Cal'd for $C_{25}H_{21}F_2N_3O_6$+H, 498.1476; Found, 498.1474. $^1H$ NMR ($CDCl_3$+1 drop $CD_3OD$, TMS):*8.890 (s, 1 H), 8.24 (d, J=13 Hz, 1 H), 8.16 (d, J=8 HZ, 1 H), 7.66 (m, 1 H), 7.52 (m, 1 H), 7.38 (m, 1 H), 4.86 (m, 1 ); 4.14 (m, 1 H), 3.89 (m, 1 H), 3.70–3.61 (m, 3 H), 2.05 (s, 3 H), 1.41 (m, 2 H), 1.25 (m, 2 H). TLC: $R_f$=0.22 (5% MeOH/$CH_2Cl_2$+1% HOAc); UV-visualized).

Ethyl 7-[4-((5S{[(tert-butoxycarbonyl)amino]methyl}-2-oxo-1,3-oxazolidin-3-yl)-2-fluorophenyl]-1-cyclopropyl-6-fluoro-4-oxo-1,4-dihydro-3-quinolinecarboxylate (Compound 9b)

A suspension of Compound 7b (380 mg., 0.898 moles), prepared as described in Kiely, J. S.; Laborde, E.,; Lesheshki, L. E.; Busch, R. A. *J. Heterocyclic Chem.* 1991, 28, 1581–1585, and Compound 8 (350 mg, 0.988 moles) in 9 mL of 1,2-dimethoxythane was degassed by repeated evacuation and flushing with nitrogen. addition of 2M $K_2HPO_4$ (0.9 mL, 1.8 moles) was made via pipette followed by addition of dichlorobis(triphenylphosphine)palladium(II) (65 mg, 0.093 moles). The resulting mixture was degassed and reflexed under nitrogen for 21 hours. The dark brown, homogeneous solution was cooled to room temperature and concentrated under reduced pressure. The crude product (685 mg) was chromatographed on a 40S Biotage column. The column was conditioned with 80% EtOAc/heptane, loaded with EtOAc (plus a small amount of $CH_2Cl_2$) and eluted with 900 mL of 80% EtOAc/heptane followed by 500 mL of EtOAc. Fractions 30–52 (20 mL cuts) were combined, evaporated and dried (house vacuum, 45E C, 3 days) to yield Compound 9b (175.5 mg, 33.5%) as a cream-colored solid. MS (ESI+) for $C_{30}H_{31}F_2N_3O_7$: m/z 584.1 $(M+H)^+$. $^1H$ NMR($CDCl_3$, TMS):*8.65 (s, 1 H); 8.23 (d,J=10.0 Hz, 1 H), 7.99 (d, J=5.8 Hz, 1 H), 7.63 (m, 1 H), 7.50 (m, 1 H), 7.36 (m, 1 H), 5.01 (m, 1 H), 4.82 (m, 1 H), 4.42 (q, J=7.1 Hz, 2 H), 4.10 (M, 1 H); 3.94 (m, 1 H); 3.58–3.50 (m, 3 H), 1.45–1.42 (m, 12 H), 1.34 (m, 2 H), 1.18 (m, 2 H). TLC: $R_f$=0.32 (5% MeOH/$CH_2Cl_2$); UV-visualization.

Ethyl 7-(4-{(5S)-5-[(acetylamino)methyl]-2-oxo-1,3-oxazolidin-3-yl}-2-fluorophenyl)-1-cyclopropyl-6-fluoro-4-oxo-1,4-dihydro-3-quinolinecarboxylate (Compound 10b)

A solution of Compound 9b (90 mg, 0.154 moles) in 2 mL of methylene chloride at 0EC was treated via syringe with trifluoroacetic acid (1.0 mL, 12.98 moles). The resulting yellow solution was stirred at 0EC for 30 minutes and at room temperature for 1 hour. TLC analysis indicated that the reaction was complete. The solvent was removed under reduced pressure, and the residue was dried under high vacuum at room temperature for 2 hours to afford ethyl-7{40[(5S)-5-(aminomethyl)-2-oxo-1,3-oxazolidin-3-yl]-2-fluorophenyl}-1-cyclopropyl-6-fluoro-4-oxo-1,4-dihydro-3-quinolinecarboxylate, trifluoroacetic acid salt (94.9 mg, quantitative) as a sticky, gold solid. MS:(ESI+) for $C_{25}H_{23}F_2N_3O_5$: m/z 484.4 $(M+H)^+$. TLC: $R_f$=0.19 (4% MeOH/$CH_2Cl_2$+1% $NH_4OH$); UV-visualization. A suspension of ethyl-7{40[(5S)-5-(aminomethyl)-2-oxo-1,3-oxazolidin-3-yl]-2-fluorophenyl}-1-cyclopropyl-6-fluoro-4-oxo-1,4-dihydro-3-quinolinecarboxylate, trifluoroacetic acid salt (94.5 mg, 0.158 moles) in 2.5 mL of pyridine at room temperature was created via syringe with acetic anhydride (640 ΦL, 6.78 moles). The resulting amber solution was stirred under nitrogen at room temperature for 1 hour. TLC analysis indicated that the reaction was complete. The solution was cooled to 0EC and quenched with 0.6 mL of methanol. After stirring under nitrogen at 0EC for 15 minutes and at room temperature for 20 minutes, the solvent was removed under reduced pressure. the crude product (112.2 mg) was chromatographed on a 14×80 mm Biotage column. The column was conditioned, loaded and eluted with 5% 4N $NH_3^-$MeOH/$CH_2Cl_2$. Fractions 6–12 (5 mL cuts) were combined, evaporated and dried under high vacuum at room temperature for 16 hours to yield Compound 10b (45.9 mg, 55%) as an off-white solid that melted at 186–187EC. MS(ESI+) for $C_{27}H_{25}F_2N_3O_6$: m/z 526.3 $(M+H)^+$.

Example 4

Synthesis of Quinolone-Isoxazolinones: 7-[2-Acetamidomethyl-2- hydroisoxazole-5-one-4-yl]-3-carboxy-1-cyclopropyl-1,4-dihydroquinoline-4-one (Compound 13)

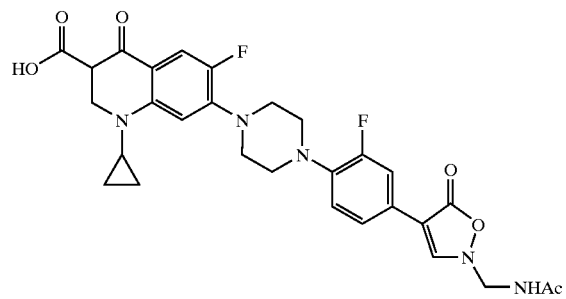

The synthesis of Compound 13 includes several steps, as described below.

tert-Butyl 4-(4-formylphenyl)piperazinecarboxylate (Compound 28)

1-(t-Butoxycarbonyl)piperazine (1.86 g, 10 mmol), p-fluorobenzaldehyde 27 (1.24 g, 10 mmol), and $K_2CO_3$ (1.74 g, 11 mmol) in dry pyridine (10 mL) are stirred at reflux under a nitrogen atmosphere for 24 h. Most of the solvent is removed under vacuum and the residue is partitioned between EtOAc (150 mL) and water (100 mL). The aqueous layer is washed with EtOAc (2×50 mL) and the combined organic layers are sequentially washed with 3% aq. citric acid (2×100 mL), water (100 mL), brine (100 mL), and dried ($MgSO_4$). The solvent is removed under vacuum and the residue washed with hexanes and dried under vacuum. The product-can be used as such, or further purified by silica gel column chromatography (dichloromethane-MeOH gradient).

Ethyl (2E)-2-(4-{4-[(tert-butyl)oxycarbonyl]piperazinyl}phenyl)-3-hydroxyprop-2-enoate (Compound 29)

The synthesis is performed in an analogous manner to that described by Mahmood et al., *J. Org. Chem.*, 63, pgs. 3333–3336 (1998). Ethyl diazoacetate (6 mmol) in dichloromethane (40 mL) is added slowly (syringe pump, about 7 h) to a solution of aldehyde 27 (1.45 g, 5 mmol) and [Fe(Cp)(CO)$_2$(THF)]BF$_4$ (0.5 mmol) in dichloromethane (60 mL) under a nitrogen atmosphere at 0° C. The mixture is stirred at 0° C. for an additional 12 h, then ethyl ether (100 mL) is added. The resulting suspension is filtered through a plug of silica gel, the solvent is removed under vacuum, and the resulting Compound 27 is purified by column chromatography.

tert-Butyl 4-[4-(5-oxo-2-hydroisoxazol-4-yl)phenyl]piperazinecarboxylate (Compound 30)

Aqueous hydroxylamine (50%, 10 mmol) and Compound 29 (4 mmol) in MeOH (70 mL) and water (18 mL) are heated under reflux for 3 h. The MeOH is removed under vacuum, and the residue triturated with water. The precipitated Compound 30 is filtered, washed with cold water, and dried under vacuum.

tert-Butyl 4-(4-{2-[(acetylamino)methyl]-5-oxo-2-hydroisoxazol-4-yl}phenyl) piperazinecarboxylate (Compound 31)

N-(Hydroxymethyl)acetamide acetate (10 mmol) is added to Compound. 30 (2 mmol) in dry dimethylformamide (18 mL), followed by K$_2$CO$_3$ (10 mmol). The mixture is stirred for 5 h, then poured into ice water, After about 18 h, the precipitated Compound 31 is filtered and dried under vacuum.

N-{[5-Oxo-4-(4-piperazinylphenyl)-2-hydroisoxazol-2-yl]methyl}acetamide (Compound 12)

Trifluoroacetic acid (2 mL) is added to a solution of Compound 31 (1 mmol) in dichloromethane (5 mL). After 30 min, dichloromethane is removed under vacuum, and the product 12 is precipitated with ethyl ether, filtered, and dried under vacuum.

7-[2-Acetamidomethyl-2- hydroisoxazole-5-one-4-yl]-3-carboxy-1-cyclopropyl-1,4-dihydroquinoline-4-one (Compound 13)

A mixture of Compound 12 (1.1 mmol) and 3-carboxy-1-cyclopropyl-7-chloro-6-fluoro-1,4-dihydroquinoline-4-one (1 mmol) in N-methylpyrrolidine-2-one (2.0 mL) and N-methylmorpholine (0.4 mL) is stirred at 110–130° C. for 48 h. The mixture is cooled to r.t., and a majority of the solvent is removed under vacuum. The residue is triturated with water, and the resulting precipitate is filtered, sequentially washed with excess water, THF, and ether, and dried under vacuum. Compound 13 is purified by preparative HPLC.

Example 5

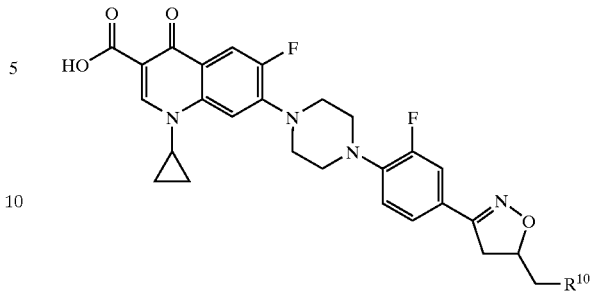

Synthesis of Quinolone-Isoxazolines

7-(5-Acetamidomethyl-4,5-dihydroisoxazole-3-yl)-3-carboxy-1 -cyclopropyl-1,4-dihydroquinoline-4-one (Compound 16, $R^{10}$=NHAc).

The synthesis of the Compound 16 includes of several steps as described below.

tert-Butyl 4-[4-((hydroxyimino)methyl)phenyl]piperazinecarboxylate (Compound 32)

A mixture of aldehyde 28 (10 mmol) and hydroxylamine hydrochloride (15 mmol) in MeOH (20 mL) with pyridine (2 mL) is stirred at r.t. for 12–15 h. The solvent is removed under vacuum, and the residue is distributed between EtOAc (100 mL) and water (30 mL). The organic layer is washed with 2% aq. citric acid (2×30 mL), water (30 mL), brine (30 mL), and dried (MgSO$_4$). The solvent is evaporated and Compound 32 dried under vacuum.

tert-Butyl 4-[4-(chloro(hydroxyimino)methyl)phenyl]piperazinecarboxylate (Compound 33)

N-Chlorosuccinimide (12 mmol) is added portionwise with stirring to a solution of aldoxiome 32 (10 mmol) in dichloromethane (50 mL) with pyridine (10 mL) at 0° C. The mixture is stirred at this temperature for 3 h, and then 1–2 h at r.t. The solvent is removed under vacuum, the residue is triturated with ice water, and the precipitated Compound 33 is sequentially washed with ice water, cold 3% aq. citric acid, water, and dried under vacuum.

tert-Butyl 4-(4-{5-[(acetylamino)methyl]-4,5-dihydroisoxazol-3-yl}phenyl) piperazinecarboxylate (Compound 34)

Triethylamine (7.5 mmol) is added dropwise with stirring to the mixture of N-acetylallylamine (7.5 mmol) and Compound 33 (5 mmol) in dichloromethane (20 mL). The mixture is stirred at r.t. overnight. The solvent is removed under vacuum, and the residue is distributed between EtOAc (100 mL) and water (30 mL). The organic layer is sequentially washed with 2% aq. citric acid (2×30 mL), water (30 mL), brine (30 mL), and dried (MgSO$_4$). The solvent is evaporated and Compound 34 is purified by silica gel column chromatography (eluent: dichloromethane-MeOH gradient).

N-{[3-(4-Piperazinylphenyl)-4,5-dihydroisoxazol-5-yl]methyl}acetamide (Compound 14)

Trifluoroacetic acid (2 mL) is added to a solution of Compound 34 (1 mmol) in dichloromethane (5 mL). After 30 min, dichloromethane is removed under vacuum, and Compound 14 is precipitated with ethyl ether, filtered, and dried under vacuum.

7-(5-Acetamidomethyl-4,5-dihydroisoxazole-3-yl)-3-carboxy-1-cyclopropyl-1,4-dihydroquinoline-4-one (Compound 16)

A mixture of Compound 14 (1.1 mmol) and 3-carboxy-1-cyclopropyl-7-chloro-6-fluoro-1,4-dihydroquinoline-4-one (1 mmol) in NMP (2.0 mL) and NMM (0.4 mL) is stirred at 110–130° C. for 48 h. The mixture is cooled to r.t., and a majority of the solvent is removed under vacuum. The residue is triturated with water, the resulting precipitate is filtered, washed with excess water, THF, ether, and dried under vacuum. Compound 16 is purified by preparative HPLC. Optionally, individual 5-(R)- and 5-(S)-enantiomers (resulting from the racemic center in the isoxazoline group) are separated by HPLC using chiral phase (such as Chiralpack AD column).

Example 6

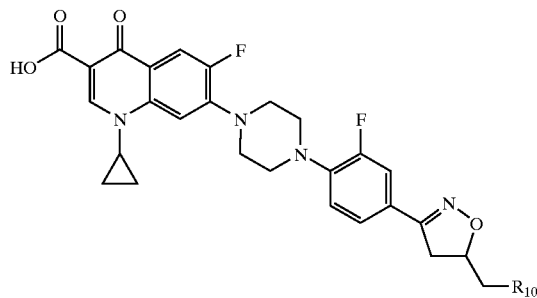

Synthesis of Quinolone-Isoxazolines: 7-(5-Hydroxymethyl-4,5-dihydroisoxazole-3-yl)-3-carboxy-1-cyclopropyl--1,4-dihydroquinoline-4-one (Compound 17, $R^{10}$=OH).

The synthesis of Compound 17 includes of several steps as described below.

tert-Butyl 4-(4-{5-hydroxymethyl-4,5-dihydroisoxazol-3-yl}phenyl) piperazinecarboxylate (Compound 35)

Triethylamine (7.5 mmol), is added dropwise with stirring to a mixture of allyl alcohol (7.5 mmol) and Compound 32 (5 mmol) in dichloromethane (20 ml). The resulting mixture is stirred at r.t. overnight. The solvent is removed under vacuum and the residue is partitioned between EtOAc (100 mL) and water (30 mL). The organic layer is washed with 2% aq. citric acid (2×30 mL), water (30 mL), brine (30 mL), and dried (MgSO$_4$). The solvent is evaporated, and Compound 35 is purified by silica gel column chromatography (eluent: dichloromethane-MeOH gradients).

3-(4-Piperazinylphenyl)-4,5-dihydroisoxazol-5-3ylmethylol (Compound 15)

Trifluoroacetic acid (2 mL) is added to a solution of Compound 35 (1 mmol) in dichloromethane (5 mL). After 30 min, dichloromethane is removed under vacuum, and Compound 15 is precipitated with ethyl ether, filtered, and dried under vacuum.

7-(5-Hydroxymethyl-4,5-dihydroisoxazole-3-yl)-3-carboxy-1-cyclopropyl-1,4-dihydroquinoline-4-one (Compound 17)

A mixture of Compound 15 (1.1 mmol) and 3-carboxy-1-cyclopropyl-7-chloro-6-fluoro-1,4-dihydroquinoline-4-one (1 mmol) in NMP (2.0 mL) and NMM (0.4 mL) is stirred at 110–130° C. for 48 h. The mixture is cooled to r.t., and a majority of the solvent is removed under vacuum. The residue is triturated with water, and the resulting precipitate filtered, sequentially washed with excess water, THF, ether, and dried under vacuum. Compound 17 is purified by preparative HPLC. Optionally, individual 5-(R)- and 5-(S)-enantiomers (resulting from the racemic center in isoxazoline group) are separated by HPLC using chiral phase (such as Chiralpack AD column).

Example 7

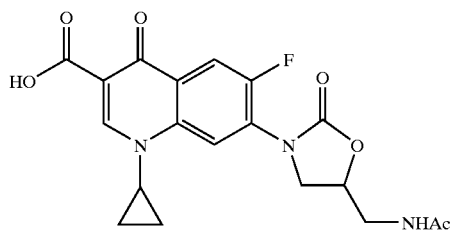

7-[5-(S)-Acetamidomethyloxazolidine-2-one-3-yl]-3-carboxy-1-cyclopropyl-6-fluoro-1,4-dihydroquinoline-4-one (Compound 19)

Compound 19 is prepared according to the General Procedure Synthesis of Quinolone-7-yl Linked Oxazolidinones from 1-acetyl-3-amino-2-(S)-oxypropylamine (2 mmol) using 3-carboxy-1-cyclopropyl-7-chloro-6-fluoro-1,4-dihydroquinoline-4-one (0.282 g, 1 mmol). The first reaction step is performed at 120–130° C. for 48 h. The mixture is cooled to room temperature (r.t.), and a majority of the solvent removed under vacuum. The resulting amino alcohol intermediate is purified by silica gel column chromatography (eluent: dichloromethane-MeOH). Cyclization is performed by dissolving the amino alcohol (1 mmol) in an aprotic organic solvent (e.g., THF or NMP) (2–5 mL), in the presence of carbonyldiimidazole (1.1 mmol) and adding imidazole (1.0 mmol). The mixture is stirred at 20–40° C. for 1–3 h. The solvent is removed under vacuum, and the product is purified by silica gel column chromatography (eluent: dichloromethane--MeOH).

Examples 8–10

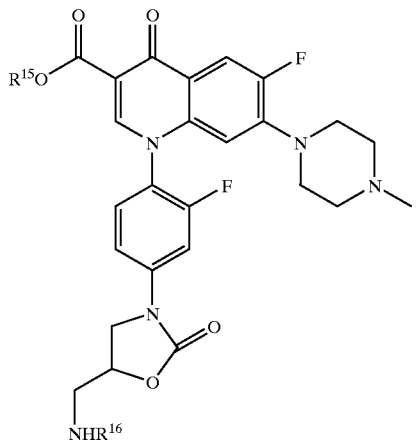

N[1]-Linked Quinolone-Oxazolidinones: 3-Carboethoxy-1-[4-(5-(S)-acetamidomethyloxazolidine-2-one-3-yl)-2-fluorophenyl]-7-(4-methylpiperazine-1-yl)-6-fluoro-1,4-dihydroquinoline-4-one (Compound 24, $R^{15}$=Et, $R^{16}$=Ac), 3-Carboxy-1-[4-(5-(S)-aminomethyloxazolidine-2-one-3-yl)-2-fluorophenyl]-7-(4-methylpiperazine-1-yl)-6-fluoro-1,4-dihydroquinoline-4-one (Compounds 25, $R^{15}$=H, $R^{16}$=H), and 3-Carboxy-1-[4-(5-(S)-acetamidomethyloxazolidine-2-one-3-yl)-2-fluorophenyl]-7-(4-methylpiperazine-1-yl)-6-fluoro-1,4-dihydroquinoline-4-one (Compound 26, $R^{15}$=H, $R^{16}$=Ac).

The synthesis of the above compounds was performed in several steps by the procedure described below.

Ethyl (2Z)-3-[(4-{5-[(acetylamino)methyl]-2-oxo(1,3-oxazolidin-3-yl)}-2-fluorophenyl)amino]-2-[(2,4,5-trifluorophenyl]carbonylprop-2-enoate (Compound 22)

Triethylamine (2.09 mL, 15 mmol) was added with stirring to a solution of 2,4,5-trifluorobenzoyl chloride (1.95 g, 10 mmol) and ethyl 3-dimethylaminoacrylate 20 (1.43 g, 10 mmol) in 1,4-dioxane (20 mL). The mixture was stirred at r.t. overnight, and solvent was removed under vacuum. The residue was dissolved in ethyl ether (100 mL) and hexanes (20 mL), and the resulting mixture was washed with water (2×100 mL), 2% aq. citric acid (2×100 mL), brine (100 mL), 2.5% aq. NaHCO$_3$ (2×100 mL), and brine (100 mL). The organic layer was dried (MgSO$_4$), and the solvents removed under vacuum to provide ethyl-2-(dimethylamino)methylene-2-(2,4,5-trifluorobenzoyl)acetate 21 as a light orange oil (Yield 2.55 g (85%). MS (m/z): 302 [M+H]$^+$. R$_t$ 4.9 min.). A solution of Compound 21 (0.301 g, 1.0 mmol) and 5-(S)-acetamidomethyl-3-(4-amino-3-fluorophenyl)-oxazolidine-2-one (0.267 g, 1.0 mmol) in EtOH (9 mL) was agitated at 40° C. for 16 h. The solvent was removed under vacuum, and the resulting residue dissolved in ethyl ether (75 mL). The ether solution was washed with 3% aq. citric acid (2×40 mL), brine (40 mL), and dried (MgSO$_4$). The solvent was removed under vacuum to afford Compound 22 as a thick light-orange oil. Yield 0.50 g (90%). MS (m/z): 524 [M+H]$^+$. R$_t$ 5.5 min.

1-(4-{5-[(acetylamino)methyl]-2-oxo(1,3-oxazolidin-3-yl)}-2-fluorophenyl)-6,7-difluoro-4-oxohydroquinoline-3-carboxylate (Compound 23)

Compound 22 (0.40 g, 0.76 mmol) was heated under a nitrogen atmosphere with 3% diazabicyclo[4.4.0]undec-2-ene in N-methylpyrrolidine-2-one (4 mL) for 30 min. at 80° C. Most of the solvent was removed under a high vacuum, and the residue partitioned between ethyl acetate (EtOAc) (50 mL) and water (30 mL). The organic layer was sequentially washed with water (30 mL), 3% aq. citric acid (2×30 mL), water (30 mL), brine (30 mL), and dried (MgSO$_4$). The solvent was removed under vacuum and the residue washed with an excess of ethyl ether to afford Compound 23 as orange crystals. Yield 0.275 g (72%). MS (m/z): 504 [M+H]$^+$. R$_t$ 4.5 min.

3-Carboethoxy-1-[4-(5-(S)-acetamidomethyloxazolidine-2-one-3-yl)-2-fluorophenyl]-7-(4-methylpiperazine-1-yl)-6-fluoro-1,4-dihydroquinoline-4-one (Compound 24) and 3-Carboxy-1-[4-(5-(S)-aminomethyloxazolidine-2-one-3-yl)-2-fluorophenyl]-7-(4-methylpiperazine-1-yl)-6-fluoro-1,4-dihydroquinoline-4-one (Compound 25)

A solution of Compound 23 (0.05 g, ca. 0.1 mmol) and 1-methylpiperazine (0.04 mL, 0.34 mmol) in N-methylpyrrolidine-2-one was heated at 80° C. for 18 h. A majority of the solvent was removed under a high vacuum, and the resulting crude Compound 24 heated with 6N aq. HCl (3 mL) in a sealed vial for 4 h at 80° C. The solvent was evaporated under vacuum to about 2 mL, and amine 25 purified by preparative RP HPLC. MS (m/z): 514 [M+H]$^+$. R$_t$ 3.5 min.

3-Carboxy-1-[4-(5-(S)-acetamidomethyloxazolidine-2-one-3-yl)-2-fluorophenyl]-7-(4-methylpiperazine-1-yl)-6-fluoro-1,4-dihydroquinoline-4-one (Compound 26)

Acetic anhydride (0.05 mL) was added to a suspension of amine 25 (0.01 g, 0.016 mmol) with poly(vinylpyridine) (0.1 g) in MeCN (3 mL). The mixture was agitated for 30 min at r.t. The supernatant was filtered, the separated resin washed with MeOH (2×3 mL), and the combined filtrates evaporated under vacuum. The resulting solid was recrystallized from a minimum of MeOH to afford Compound 26 as white crystals. Yield 6.9 mg (64%). MS (m/z): 556 [M+H]$^+$. R$_t$ 3.7 min.

As shown in Table 1, the compounds of Example 1, 2 and 3 demonstrated a potent antibacterial activity.

TABLE 1

Antibacterial Activity of Selected Examples

| | MIC(:g/mL) | | | | | |
|---|---|---|---|---|---|---|
| Example No. | E. faecalis UC9217 | S. aureus UC9218 | S. pneumoniae UC9912 | H. influenzae UC30063 | M. catarrhalis UC30607 | E. coli UC6674 |
| 1 | 0.25 | 0.5 | 0.125 | 8 | 1 | 16 |
| 2 | 0.5 | 1 | 0.25 | 4 | 2 | 16 |
| 3 | 8 | 2 | 4 | 0.5 | 4 | 4 |

The compounds of the invention can be used for the treatment or prevention of infectious disorders caused by variety of bacterial organisms. Examples include Gram positive and Gram negative aerobic and anaerobic bacteria, including *Staphylococci*, for example *S. aureus*; *Enterococci*, for example *E. faecalis*; *Streptococci*, for example *S. pneumoniae*; *Haemophilis*, for example *H. influenza*; *Moraxella*, for example *M. catarrhalis*; and *Escherichia* for example *E. coli*. Other examples include *Mycobacteria*, for example *M. tuberculosis*; intercellular microbes, for example *Chlamydia* and *Rickettsiae*; and *Mycoplasma*, for example *M. pneumoniae*.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structural formula:

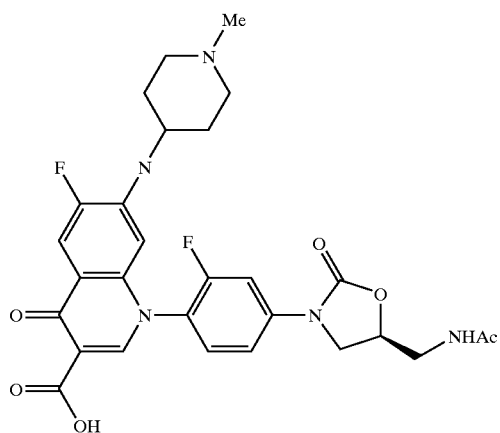

or a pharmaceutically acceptable salt, hydrate, or prodrug thereof.

2. A compound selected from the group consisting of 2-methyipropyl (4-bromo-3-fluorophenyl)carbamate, (5R)-3-(4-bromo--3-fluorophenyl)-5-(hydroxymethyl)-1,3-oxazolidin-2-one, [(5R)-3-(4-bromo-3-fluorophenyl)-2-oxo-1,3-oxazolidin-5-yl]methyl 3-nitrobenzene sulfonate, and tert-butyl [(5S)-3-(4-bromo-3-fluorophenyl)-2-oxo-1,3-oxazolidin-5-yl]methylcarbamate.

3. A compound having a general structure formula.

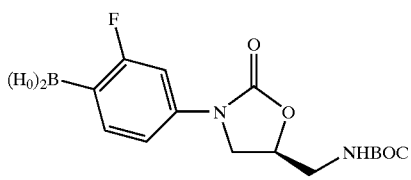

or a salt or hydrate thereof.

4. A method of preparing a boronic acid having a general structural formula:

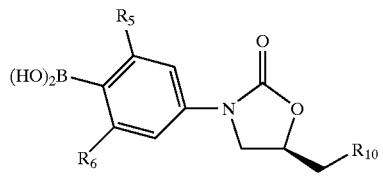

wherein $R^5$ and $R^6$ are independently selected from the group consisting of H, methyl, hydroxy, and halo; $R^{10}$ is selected from the group consisting of OH, alkoxy, aryloxy, and NHC(=Z)$R^{11}$; $R^{11}$ is selected from the group consisting of H, $C_1$–$C_7$alkyl, $C_3$–$C_5$cycloalkyl, hydroxymethyl, haloalkyl, $CH_2SMe$, $NR^{12}_2$, $C_1$–$C_4$alkoxy, and aryloxy; $R^{12}$ is $C_1$–$C_4$alkyl; and Z is O or S, or a salt or hydrate thereof, comprising contacting an haloaryloxazolidinone having a general structural formula:

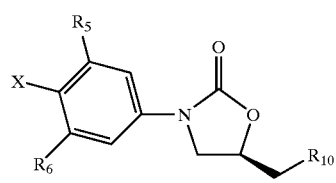

wherein X is halogen, with an alkaline base whose conjugate acid has a pKa of greater than about 10 and an alkylborate.

5. The method of claim 4, wherein the alkylborate is trimethylborate.

* * * * *